US010787658B2

(12) United States Patent
Heggeness

(10) Patent No.: US 10,787,658 B2
(45) Date of Patent: Sep. 29, 2020

(54) MAMMALIAN PLURIPOTENT STEM CELLS, METHODS FOR THEIR PRODUCTION, AND USES THEREOF

(71) Applicant: University of Kansas, Lawrence, KS (US)

(72) Inventor: Michael H. Heggeness, Wichita, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 16/375,006

(22) Filed: Apr. 4, 2019

(65) Prior Publication Data

US 2019/0218543 A1  Jul. 18, 2019

Related U.S. Application Data

(63) Continuation of application No. 14/816,661, filed on Aug. 3, 2015, now abandoned.

(60) Provisional application No. 62/032,911, filed on Aug. 4, 2014.

(51) Int. Cl.
   *C12N 5/074* (2010.01)
   *C12N 13/00* (2006.01)
   *C12N 5/0797* (2010.01)

(52) U.S. Cl.
   CPC .......... *C12N 13/00* (2013.01); *C12N 5/0607* (2013.01); *C12N 5/0623* (2013.01); *C12N 2501/155* (2013.01); *C12N 2506/08* (2013.01)

(58) Field of Classification Search
   None
   See application file for complete search history.

(56) References Cited

U.S. PATENT DOCUMENTS

| | | | |
|---|---|---|---|
| 2003/0003572 | A1 | 1/2003 | Anderson et al. |
| 2011/0110899 | A1 | 5/2011 | Shi et al. |
| 2011/0154518 | A1 | 6/2011 | Kim et al. |
| 2012/0128655 | A1 | 5/2012 | Kim et al. |
| 2012/0269782 | A1 | 10/2012 | Guo et al. |
| 2012/0270313 | A1 | 10/2012 | Paul et al. |
| 2013/0034858 | A1 | 2/2013 | Inoue et al. |
| 2013/0089885 | A1 | 4/2013 | Kang et al. |
| 2015/0159135 | A1 | 6/2015 | Davis et al. |
| 2019/0218543 | A1* | 7/2019 | Heggeness ............ C12N 5/0623 |

FOREIGN PATENT DOCUMENTS

| | | |
|---|---|---|
| CN | 101492676 | 7/2009 |
| CN | 102191221 | 9/2011 |
| WO | 2000/52143 A2 | 9/2000 |
| WO | 2011/013806 A1 | 2/2011 |
| WO | 2013/188744 A1 | 12/2013 |

OTHER PUBLICATIONS

Extended European Search Report, dated Dec. 14, 2017, in connection with Application No. 15829472.8.
International Search Report dated Nov. 4, 2015 in connection with PCT/US2015/043424.
Written Opinion of the International Searching Authority dated Nov. 4, 2015 in connection with PCT/US2015/043424.
Carragee et al., 2011, "A critical review of recombinant human bone morphogenetic protein-2 trials in spinal surgery: emerging safety concerns and lessons learned," The Spine Journal 11:471-491.
Croes et al., 2015, "Proinflammatory Mediators Enhance the Osteogenesis of Human Mesenchymal Stem Cells after Lineage Commitment," PLoS One 10(7):e0132781.
Danova-Alt et al., 2012, "Very Small Embryonic-Like Stem Cells Purified from Umbilical Cord Blood Lack Stem Cell Characteristics," PLoS One 7(4):e34899.
Davis et al., 2013, "Stem Cell Gene Therapy," Chapter 77 in Handbook of Stem Cells, published by Elsevier Inc., pp. 937-949.
Dmitriev et al., 2011, "Bone morphogenetic protein-2 and spinal arthrodesis: the basic science perspective on protein interaction with the nervous system," The Spine Journal 11:500-505.
Heggeness, 2011, "Commentary: Important considerations on bone morphogenetic protein-2 and neuroinflammation," The Spine Journal 11:506.
Heggeness, et al., 2017, "Quiescent pluripotent stem cells reside within murine peripheral nerves that can be stimulated to proliferate by recombinant human bone morphogenic protein 2 or by nerve trauma," The Spine Journal 17:252-59.
Kim, et al., 2009, "Oct4-Induced Pluripotency in Adult Neural Stem Cells," Cell 136:411-19.
Krause et al., 2001, "Multi-Organ, Multi-Lineage Engraftment by a Single Bone Marrow-Derived Stem Cell," Cell 105:369-377.
Lazard et al., 2011, "Cell-Based Gene Therapy for Repair of Critical Size Defects in the Rat Fibula," Journal of Cellular Biochemistry 112:1563-1571.
Lazard et al., 2015, "Osteoblasts Have a Neural Origin in Heterotopic Ossification," Clin Orthop Relat Res 73(9):2790-806.
Liao et al., 2009, "Generation of Induced Pluripotent Stem Cell Lines from Adult Rat Cells," Cell Stem Cell 4:11-15.
Liu et al., 2008, "Generation of Induced Pluripotent Stem Cells from Adult Rhesus Monkey Fibroblasts," Cell Stem Cell 3:587-590.
Miyanishi et al., 2013, "Do Pluripotent Stem Cells Exist in Adult Mice as Very Small Embryonic Stem Cells?," Stem Cell Reports 1:198-208.
Okano et al., 2013, "Steps Toward Safe Cell Therapy Using Induced Pluripotent Stem Cells," Circulation Research 112(3):523-33.
Olmsted-Davis et al., 2007, "Hypoxic Adipocytes Pattern Early Heterotopic Bone Formation," American Journal of Pathology 170(2):620-632.
Real et al., 2005, "The instability of the neural crest phenotypes: Schwann cells can differentiate into myofibroblasts," Int. J. Dev. Biol. 49: 151-159.

(Continued)

*Primary Examiner* — Michael D Burkhart
(74) *Attorney, Agent, or Firm* — Hovey Williams LLP

(57) ABSTRACT

The disclosure relates to nerve derived adult pluripotent stem cells characterized by expression of Oct4, Sox2, c-Myc, and Klf4, methods for obtaining them, and their use.

17 Claims, 12 Drawing Sheets

Specification includes a Sequence Listing.

(56) References Cited

OTHER PUBLICATIONS

Roelandt et al., 2013, "Multipotent Adult Progenitor Cells," Chapter 44 in Handbook of Stem Cells, published by Elsevier Inc., pp. 503-511.
Salisbury et al., 2011, "Sensory Nerve Induced Inflammation Contributes to Heterotopic Ossification," Journal of Cellular Biochemistry 112:2748-2758.
Siebel-Blum et al., 2004, "Pluripotent Neural Crest Stem Cells in the Adult Hair Follicle," Developmental Dynamics 231:258-269.
Singh et al., 2013, "The Molecular Circuitry Underlying Pluripotency in Embryonic Stem Cells and iPS Cells," Chapter 5 in Handbook of Stem Cells, published by Elsevier Inc., pp. 29-35.
Staff Report on Medtronic's Influence on Infuse Clinical Trials, prepared by the staff of the Committee on Finance United States Senate Oct. 2012.
Szade et al., 2013, "Murine Bone Marrow Lin- 2Sca-1+ CD45- Very Small Embryonic-Like (VSEL) Cells Are Heterogeneous Population Lacking Oct-4A Expression," PLoS One 8(5):e63329.
Takahashi et al., 2006, "Induction of Pluripotent Stem Cells from Mouse Embryonic and Adult Fibroblast Cultures by Defined Factors," Cell 126:663-676.
Takahashi et al., 2007, "Induction of Pluripotent Stem Cells from Adult Human Fibroblasts by Defined Factors," Cell 131:861-872.
Trounson, 2009, "Rats, Cats, and Elephants, but Still No Unicorn: Induced Pluripotent Stem Cells from New Species," Cell Stem Cell 4:3-4.
Wang et al., 2014, "State-of-the-art human gene therapy: part I. Gene delivery technologies," HHS Public Access author manuscript, published in final form as Discov Med. 18(97): 67-77.
Wang et al., 2014, "State-of-the-art human gene therapy: part II. Gene therapy strategies and applications," HHS Public Access author manuscript, published in final form as Discov Med. 18(98): 151-161.
Widera et al., 2011, "Schwann Cells Can Be Reprogrammed to Multipotency by Culture," Stem Cells and Development 20(12):2053-2064.
Yamanaka, 2008, "Induction of pluripotent stem cells from mouse fibroblasts by four transcription factors," Cell Prolif. 41 (Suppl. 1):51-56.
Yamanaka, 2009, "A Fresh Look at iPS Cells," Cell 137:13-17.
Yang et al., 2016, "Differentiation of nerve-derived adult pluripotent stem cells into osteoblastic and endothelial cells," The Spine Journal 17:277-81.
Zaehres et al, 2007, "Induction of Pluripotency: From Mouse to Human," Cell 131:834-835.
Office Action dated Jul. 23, 2019 in connection with Japanese Patent Application No. 2017-506339.
Office Action dated Oct. 4, 2019 issued in connection with European Patent Application No. 15829472.8.
Search Report and Office Action dated Nov. 6, 2019 in connection with Chinese Patent Application No. 201580050219.5.
Parfejevs et al., 2018, "Injury-activated glial cells promote wound healing of the adult skin in mice," Nature Communications, 9(1):236.

* cited by examiner

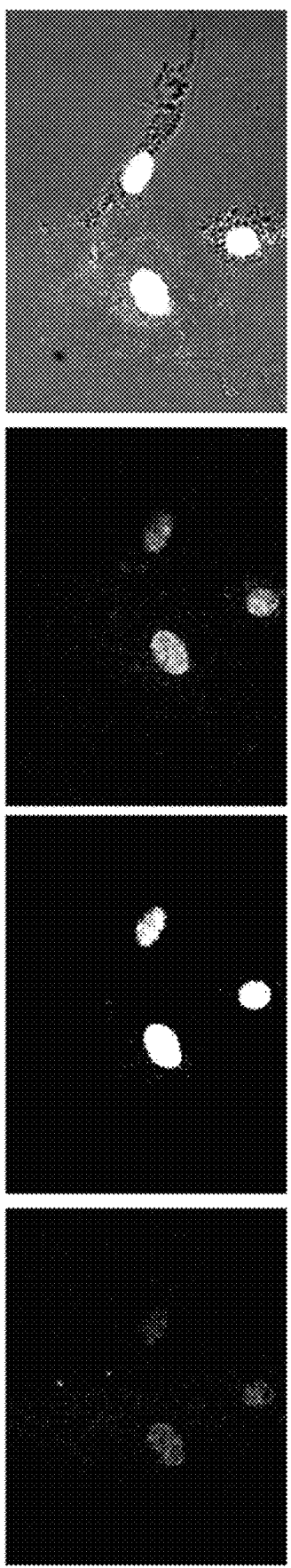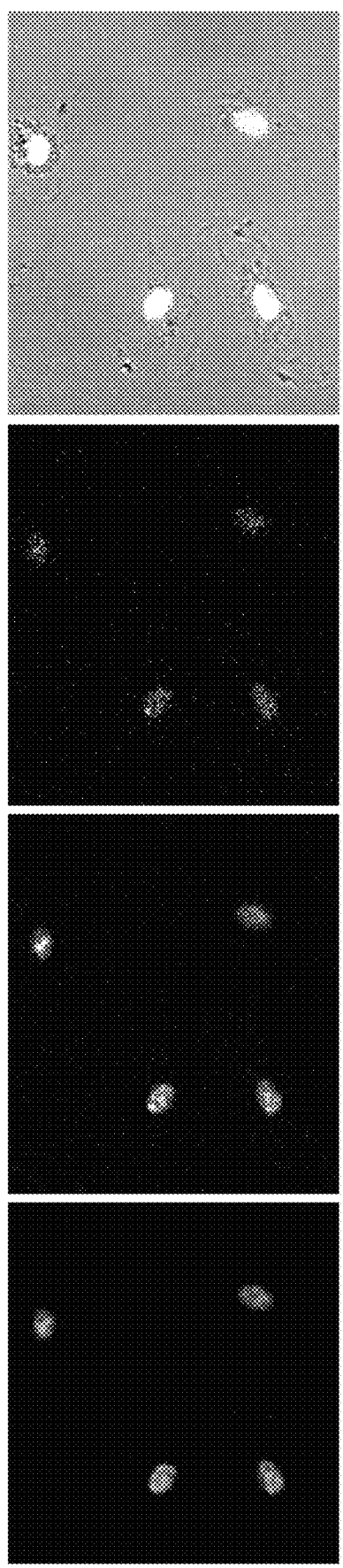
FIG. 3
FIG. 4

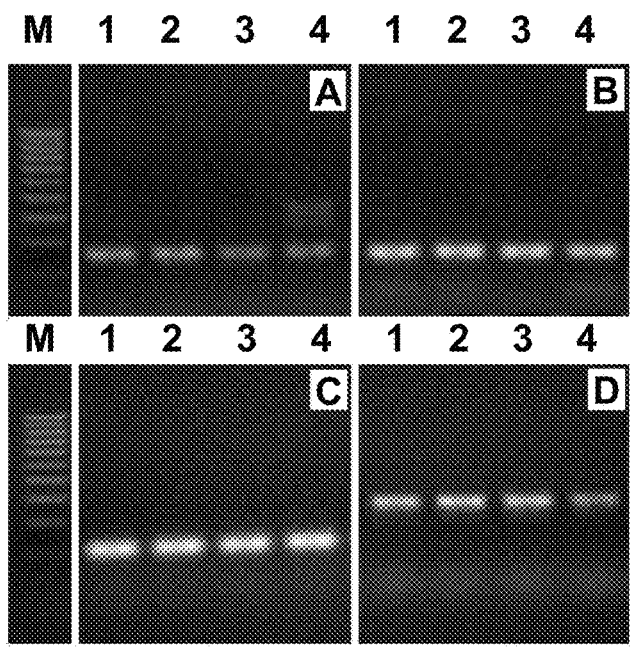
FIG. 9
FIG. 10
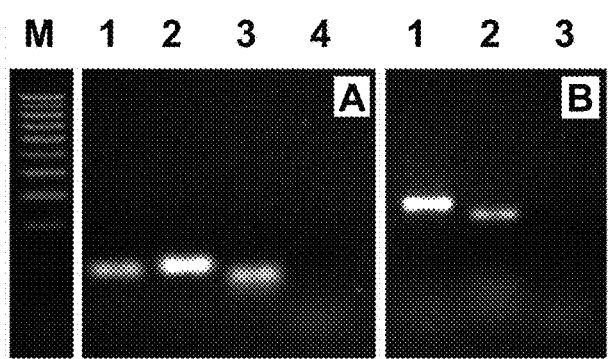
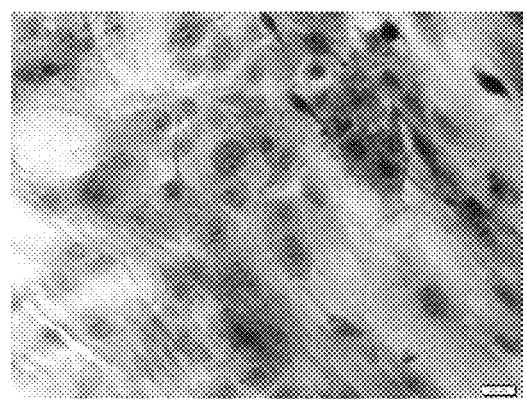
FIG. 11
FIG. 12

SEQUENCE LISTING

```
<160> NUMBER OF SEQ ID NOS: 12

<210> SEQ ID NO 1
<211> LENGTH: 20
<212> TYPE: DNA
<213> ORGANISM: Mus musculus

<400> SEQUENCE: 1
aagggttctt gctgggtttt                                          20
```

```
<210> SEQ ID NO 2
<211> LENGTH: 20
<212> TYPE: DNA
<213> ORGANISM: Mus musculus

<400> SEQUENCE: 2
agaccacgaa aacggtcttg                                               20

<210> SEQ ID NO 3
<211> LENGTH: 20
<212> TYPE: DNA
<213> ORGANISM: Mus musculus

<400> SEQUENCE: 3
acccgctcaa cgacagcagc                                               20

<210> SEQ ID NO 4
<211> LENGTH: 20
<212> TYPE: DNA
<213> ORGANISM: Mus musculus

<400> SEQUENCE: 4
ccgtggggag gactcggagg                                               20

<210> SEQ ID NO 5
<211> LENGTH: 20
<212> TYPE: DNA
<213> ORGANISM: Mus musculus

<400> SEQUENCE: 5
ctgaacagca gggactgtca                                               20

<210> SEQ ID NO 6
<211> LENGTH: 20
<212> TYPE: DNA
<213> ORGANISM: Mus musculus

<400> SEQUENCE: 6
gtgtgggtgg ctgttctttt                                               20

<210> SEQ ID NO 7
<211> LENGTH: 20
<212> TYPE: DNA
<213> ORGANISM: Mus musculus

<400> SEQUENCE: 7
gaggagtccc aggacatgaa                                               20

<210> SEQ ID NO 8
<211> LENGTH: 20
<212> TYPE: DNA
<213> ORGANISM: Mus musculus

<400> SEQUENCE: 8
agatggtggt ctggctgaac                                               20

<210> SEQ ID NO 9
<211> LENGTH: 20
<212> TYPE: DNA
<213> ORGANISM: Mus musculus

<400> SEQUENCE: 9
ccaaggcctc catgaagata                                               20
```

```
<210> SEQ ID NO 10
<211> LENGTH: 20
<212> TYPE: DNA
<213> ORGANISM: Mus musculus

<400> SEQUENCE: 10
atactgtcag gggctggttg                                              20

<210> SEQ ID NO 11
<211> LENGTH: 20
<212> TYPE: DNA
<213> ORGANISM: Mus musculus

<400> SEQUENCE: 11
ttctggactc tccctgccta                                              20

<210> SEQ ID NO 12
<211> LENGTH: 20
<212> TYPE: DNA
<213> ORGANISM: Mus musculus

<400> SEQUENCE: 12
tctgtctggc tgtcatctgg                                              20
```

MAMMALIAN PLURIPOTENT STEM CELLS, METHODS FOR THEIR PRODUCTION, AND USES THEREOF

2. CROSS-REFERENCE TO RELATED APPLICATIONS

This application is a continuation of U.S. application Ser. No. 14/816,661, filed Aug. 3, 2015, which claims the priority benefit of U.S. provisional application No. 62/032,911, filed Aug. 4, 2014, the contents of which are incorporated herein in their entireties by reference thereto.

1. STATEMENT REGARDING FEDERALLY SPONSORED RESEARCH OR DEVELOPMENT

This invention was made with government support under grant no. W911NF-13-1-0427 awarded by the U.S. Army Research Office. The government has certain rights in the invention.

3. SEQUENCE LISTING

The instant application contains a Sequence Listing which has been submitted electronically in ASCII format and is hereby incorporated by reference in its entirety. Said ASCII copy, created on Jul. 31, 2015, is named KNS-001_SL.txt and is 2,057 bytes in size.

4. BACKGROUND

Stem cells are partially or fully undifferentiated cells found in most, if not all, multi-cellular organisms. Stem cells have the ability to self-renew through mitotic cell division and to differentiate into a diverse range of specialized cell types, including but not limited to brain, bone, cartilage, glands, muscle, liver, skin, blood vessels, neural, and blood cells. Because stem cells have the potential of developing into specific types of cells and can proliferate more-or-less indefinitely or undergo renewal for extended periods of time, they hold particular potential in the context of therapeutic applications. Stem cells, whether they are pluripotent or multipotent, may be used for organ repair and replacement, cell therapies for a variety of diseases including degenerative diseases, gene therapy, and testing of new drugs for toxicities or desired activities.

However, available sources of stem cells, as well as more differentiated cells, useful for experimental and therapeutic applications have been limited, often of poor quality, unsuitable for therapy, and controversial. For example, the use of embryonic stem cells (ESCs) for human therapies is hampered by ethical issues as well as the risk that cells derived from an embryonic source may be rejected by a patient's immune system. A third problem with the use of ESCs is that ESCs are capable of forming tumors called teratomas. Teratomas contain several different cell types and often include hair, teeth, and skin. Such tumors are technically benign but can present very significant problems. An alternative to ESCs is induced Pluripotent Stem Cells (iPS cells or IPSCs). iPS cells are created by introducing genetic material into the nucleus of a differentiated "adult" cell to force expression of 4 transcription factors that govern the embryonic phenotype, namely c-Myc, Klf4, Sox2, and Oct4. Takakashi K. and Yamanaka S., *Cell* (2006) 126(4):663-76; Takahashi et al., *Cell* (2007) 131(5): 861-872. The genes are often introduced using retrovirus or lentivirus vectors. The vectors that are used to induce the cell to change into an iPS cell become integrated into the host cell genome. These events cause the cell to behave like an embryonic stem cell. iPS cells also have the potential problems identified above, most notably immune rejection, but in addition have the real risk of differentiating into malignant tumors of various types because of the genetic manipulation. Transgenes are largely silenced in iPS cells, but the late reactivation of such transgenes is possible. A significant concern is that the transgene encoding c-Myc could lead to tumorigenesis. Yamanaka S, *Cell* (2009)137(1):13-17.

Thus, there is a need for stem cells that avoid the problems of ESCs and iPS cells.

5. SUMMARY

The present disclosure provides Nerve derived adult pluripotent stem cells (referred to herein as NEDAPS cells), methods for obtaining them, cells differentiated therefrom, and uses of the NEDAPS cells and their differentiated progeny. The NEDAPS cells express Oct4, Sox2, c-Myc, and Klf4, which are four transcription factors that are markers of embryonic and pluripotent stem cells. The NEDAPS cells described here can be derived from peripheral nerves and, without being bound by any particular theory of operation, appear to represent the result of specific stimulation of a reservoir of quiescent cells that transform into NEDAPS cells. These cells can differentiate into a wide variety of cell types as described herein, are not derived from an embryonic source, and do not require the manipulation of, or introduction of, new genetic material to the NEDAPS cell nucleus. Such cells can be safely harvested from a subject exposed to NEDAPS cell proliferation conditions or from a nerve exposed to NEDAPS cell proliferation conditions ex vivo. The NEDAPS cells can be cultured in vitro or ex vivo, and propagated with or without differentiation for use in medical, veterinary, or industrial applications. For instance, NEDAPS cells can be harvested from a subject, cultured and propagated in vitro, and then reimplanted in the subject if the subject is in need of stem cell therapy. without expected risk of immune rejection of these self-derived cells. NEDAPS cells can be used for tissue repair or they can be completely or partially differentiated in culture. When implanted following complete differentiation, the progeny of the NEDAPS cells can develop into a selected tissue or organ (e.g., liver tissue) in situ. Autologous implantation of NEDAPS cells or their differentiated progeny circumvents issues associated with harvesting ESCs from embryos and circumvents immune rejection responses associated with implantation of donor tissue. Use of NEDAPS cells and their progeny is also expected to eliminate or drastically reduce the risk of teratoma formation and malignancy in transplant or stem cell therapies.

6. BRIEF DESCRIPTION OF THE FIGURES

FIGS. 1A-1N: FIG. 1A shows a normal mouse sciatic nerve (control) surgically excised and stained with hematoxylin and eosin. FIG. 1B shows a mouse sciatic nerve, surgically excised 24 hours after exposure to BMP2 by percutaneous injection, stained with hematoxylin and eosin. Note the proliferation of cells. FIG. 1C shows a mouse sciatic nerve 48 hours after exposure to BMP2 by injection, stained with H&E stain. Note the exuberant proliferation of cells. FIG. 1D shows a mouse sciatic nerve 24 hours after exposure to BMP2, stained for Oct4. FIG. 1E shows a mouse sciatic nerve 24 hours after exposure to BMP2, stained for nanog. FIG. 1F shows a mouse sciatic nerve 24 hours after exposure to BMP2, stained for Sox2. Note the proliferation of cells, the majority of which are expressing Sox2. FIG. 1G shows a mouse sciatic nerve 24 hours after exposure to BMP2, stained for Klf4. Note the proliferation of cells, the majority of which are expressing Klf4. FIG. 1H shows a mouse sciatic nerve 24 hours after exposure to BMP2, stained for Interleukin 1, an inflammatory marker. FIG. 1I shows a mouse sciatic nerve 72 hours after exposure to BMP2, stained for Oct4. Note the proliferation of cells, the majority of which are expressing Oct4. FIG. 1J shows a mouse sciatic nerve 48 hours after exposure to BMP2, stained with Sox2. Note the proliferation of cells, the majority of which are expressing Sox2. FIG. 1K shows a mouse sciatic nerve 72 hours after exposure to BMP2, stained for Sox2. Note the proliferation of cells, the majority of which are expressing Sox2. FIG. 1L shows a mouse sciatic nerve 72 hours after exposure to BMP2, stained for Oct4. Note the proliferation of cells, the majority of which are expressing Oct4. FIG. 1M shows a mouse sciatic nerve 72 hours after exposure to BMP2, stained for c-Myc. Note the proliferation of cells, the majority of which are expressing c-Myc. FIG. 1N shows a mouse sciatic nerve 24 hours after exposure to BMP2, stained for c-Myc. Note the proliferation of cells, the majority of which are expressing c-Myc.

FIGS. 2A-2F: FIG. 2A shows a normal mouse sciatic nerve in a tissue specimen from an untreated (control) mouse stained for Oct4. Oct4 is not expressed in the unstimulated nerve. FIG. 2B shows a mouse sciatic 24 hours after direct exposure to BMP2 by intramuscular (IM) injection stained for Oct4. Note the exuberant cell proliferation and the markedly abnormal nerve. The nuclei of the proliferating cells are densely stained for this stem cell marker. FIG. 2C shown a normal mouse sciatic nerve in a tissue specimen from an untreated (control) mouse stained for c-Myc. c-Myc expression is only minimally expressed in the unstimulated nerve. FIG. 2D shows a histologic section of mouse sciatic nerve and surrounding tissue 24 hours after BMP2 injection, stained for c-Myc. Note the exuberant cellular proliferation, and dense nuclear peroxidase staining for c-Myc in the proliferating cells. FIG. 2E shows a normal mouse sciatic nerve from an untreated (control) mouse stained for Klf4. The unstimulated shows no expression of Klf4. FIG. 2F shows an oblique section through the sciatic nerve in a mouse hamstring muscle harvested 48 h after IM BMP2 injection, stained for Klf4. Note the exuberant cellular proliferation and migration through tissue planes, and the positive peroxidase staining for Klf4. FIG. 2G shows the remains of a mouse sciatic nerve 72 h after exposure to BMP2 by IM injection, after immunostaining for Sox2. Note the loss of integrity of the nerve and the dense nuclear peroxidase staining.

FIG. 3 shows cultured NEDAPS cells produced using mechanical compression stained for the nonspecific nuclear stain DAPI (left panel), Sox2 (second panel from left), and c-Myc (third panel from left). The right panel is an overlay of the DAPI, Sox2 and c-Myc images.

FIG. 4 shows NEDAPS cells produced using mechanical compression stained for the nonspecific nuclear stain DAPI (left panel), Sox2 (second panel from left), and Oct4 (third panel from left). The right panel is an overlay of the DAPI, Sox2 and Oct4 images.

FIG. 9 shows PCR gels demonstrating the expression of Oct4, Sox2, c-Myc, and Klf4 in NEDAPS cells. M displays molecular weight markers; Oct4, Sox2, c-Myc, and Klf4 PCR products are shown in panels A-D, respectively. Lanes 1-2 in each panel display PCR products from duplicate preparations of nerves stimulated by simple mechanical compression and harvested at 48 hours, and lanes 3-4 in each panel display PCR products from duplicate preparations of nerves exposed to rhBMP2 by direct application in vivo and harvested at 48 hours.

FIG. 10 is a plain micrograph showing the typical morphology of NEDAPS cells grown in restrictive stem cell media. Note the flattened cell shape and adherence to substrate. This morphology is distinctly different from embryonic stem cells, which are typically round and minimally adherent to substrate.

FIG. 11 shows a PCR gel demonstrating the expression of markers of osteoblast and endothelial differentiation in NEDAPS cells that had been cultured in media to induce osteoblastic and endothelial cells, respectively. M displays molecular weight markers; Lanes 1-4 of panel A show osteopontin, type I collagen, osteocalcin, and a negative control PCR product, respectively. Lanes 1-3 of panel B show Flt-1, Flk-1, and a negative control PCR product, respectively.

FIG. 12 shows a confluent culture of NEDAPS cells that had been cultured in osteogenic culture media to induce differentiation into osteoblasts after staining for alkaline phosphatase activity (marker of osteoblastic differentiation). Note the accumulation of dye indicating the presence of this enzymatic activity which is characteristic of osteoblasts.

Figure 13:
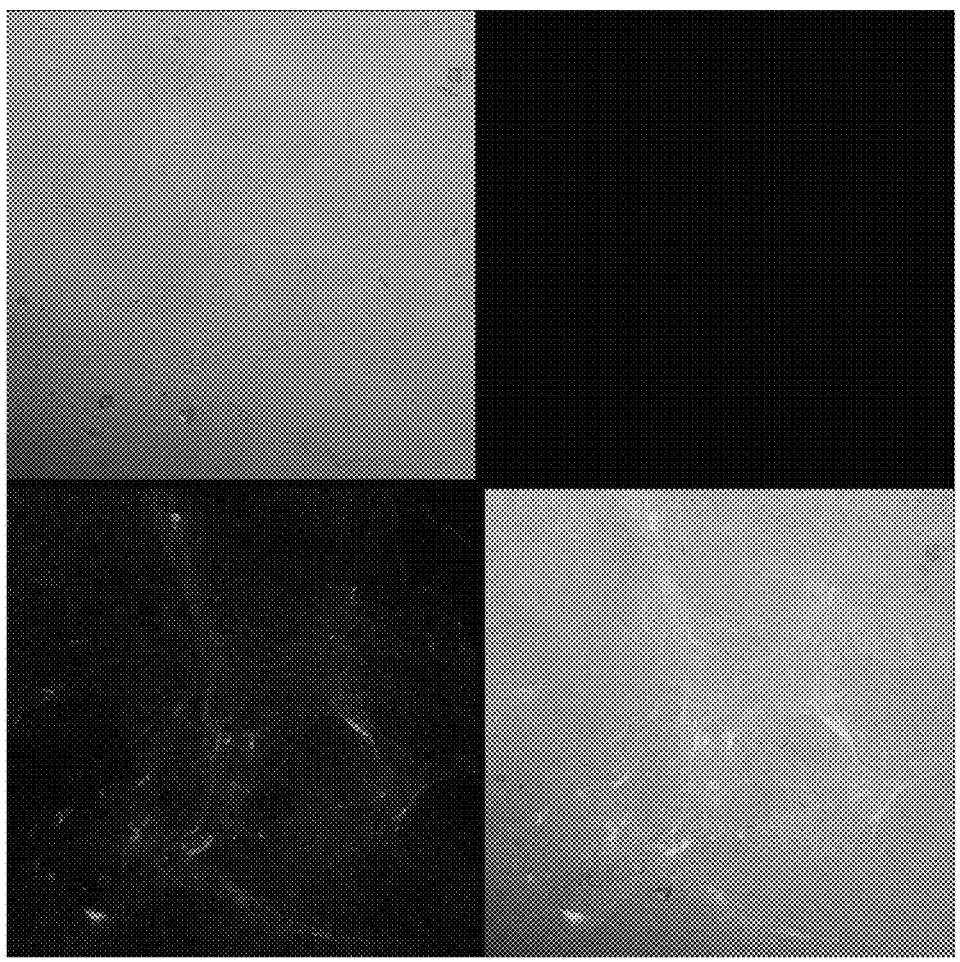

FIG. 13 shows NEDAPS cells cultured in osteogenic media. The upper left panel shows cells after fluorescence immunostaining for the osteoblast marker type I collagen. The upper right panel shows the same field as the upper left panel imaged with Nomarski optics. The bottom left panel shows a composite of the immunostained and the Nomarski images. The bottom right panel is blank.

Figure 14:
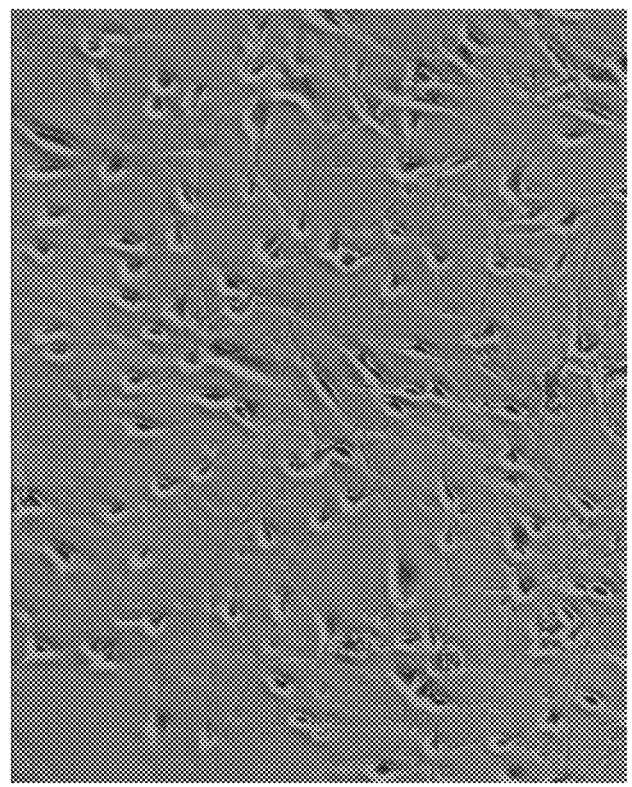

FIG. 14 is a plain micrograph of NEDAPS cells that have been induced to differentiate into an endothelial phenotype. The round appearance of the cell bodies and long narrow processes are typical of cultured endothelial cells before they become confluent, after which the array of rounded cell bodies displays a "cobblestone" appearance.

Figure 15:
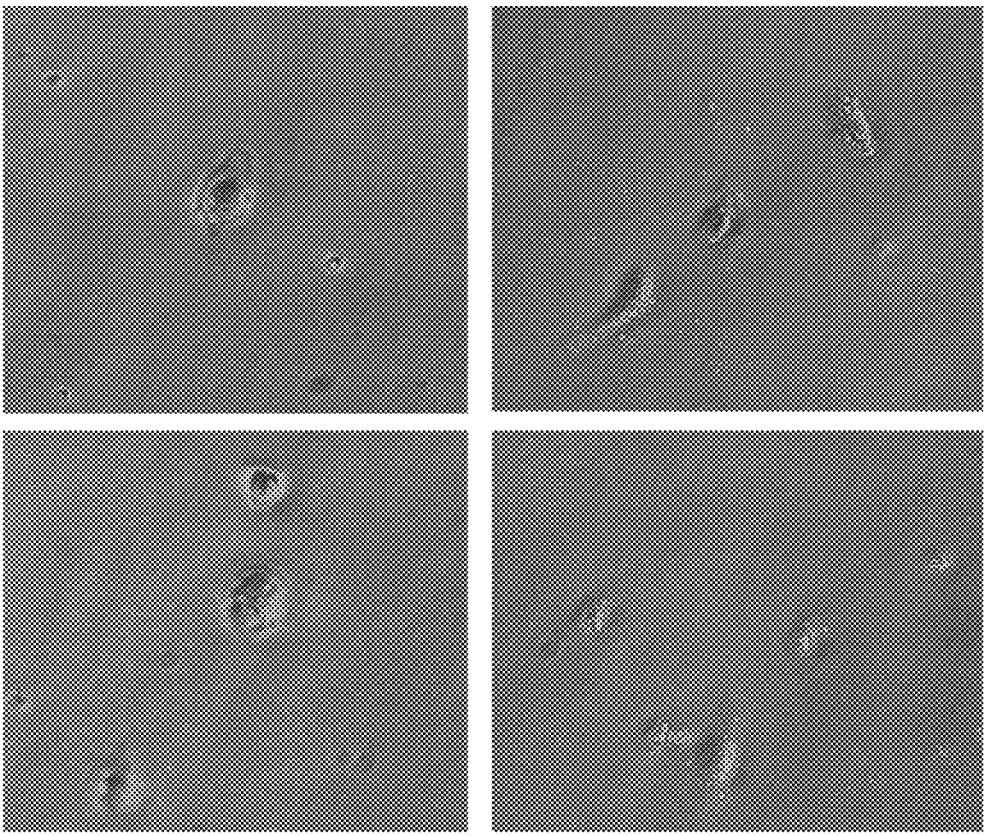

FIG. 15 shows four different micrographs of NEDAPS cells that have been cultured in an endodermal differentiation medium. Note that the morphology of these differentiated cells is quite distinct from the NEDAPS cells from which they were derived, displaying a more rounded shape, with a less intimate adherence to the substrate, and larger nuclei.

Figure 16:
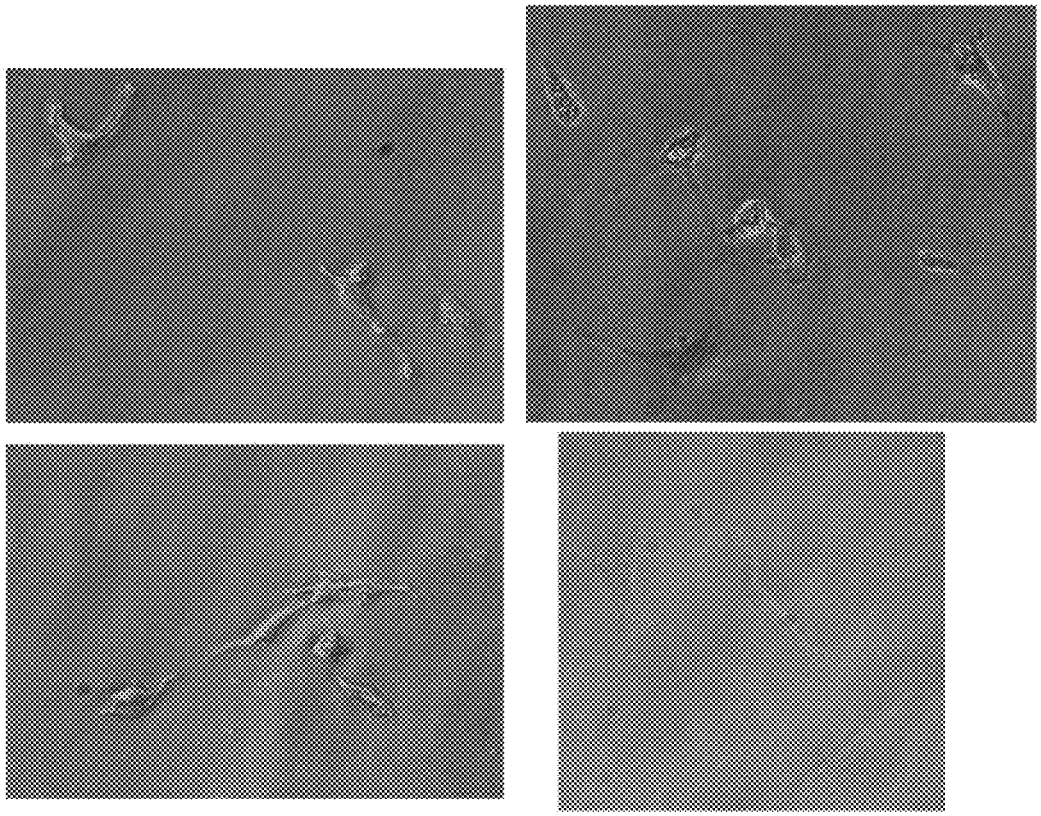

FIG. 16 shows four different micrographs of NEDEL cells that have been cultured in an ectoderm differentiation medium. Note that these cells are morphologically quite distinct from the NEDAPS cells from which they were derived, displaying elongated cell shapes consistent with developing nerve tissue.

Figure 17:
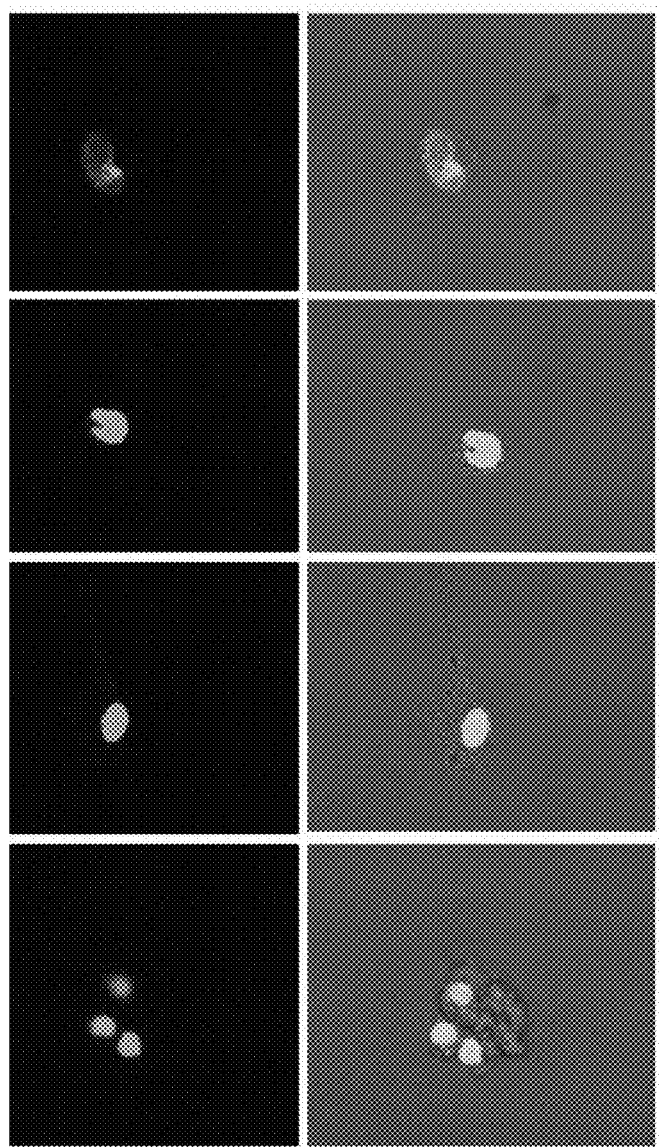

FIG. 17 shows NEDAPS cells produced by stimulating an excised nerve ex vivo. The upper panels show, from left to right, cells immunostained for Klf4, Sox2, Oct4, and c-Myc. The lower panels show the overlays of the fluorescent signals shown in the upper panels on the bright-field images of the same cells.

Figure 18:
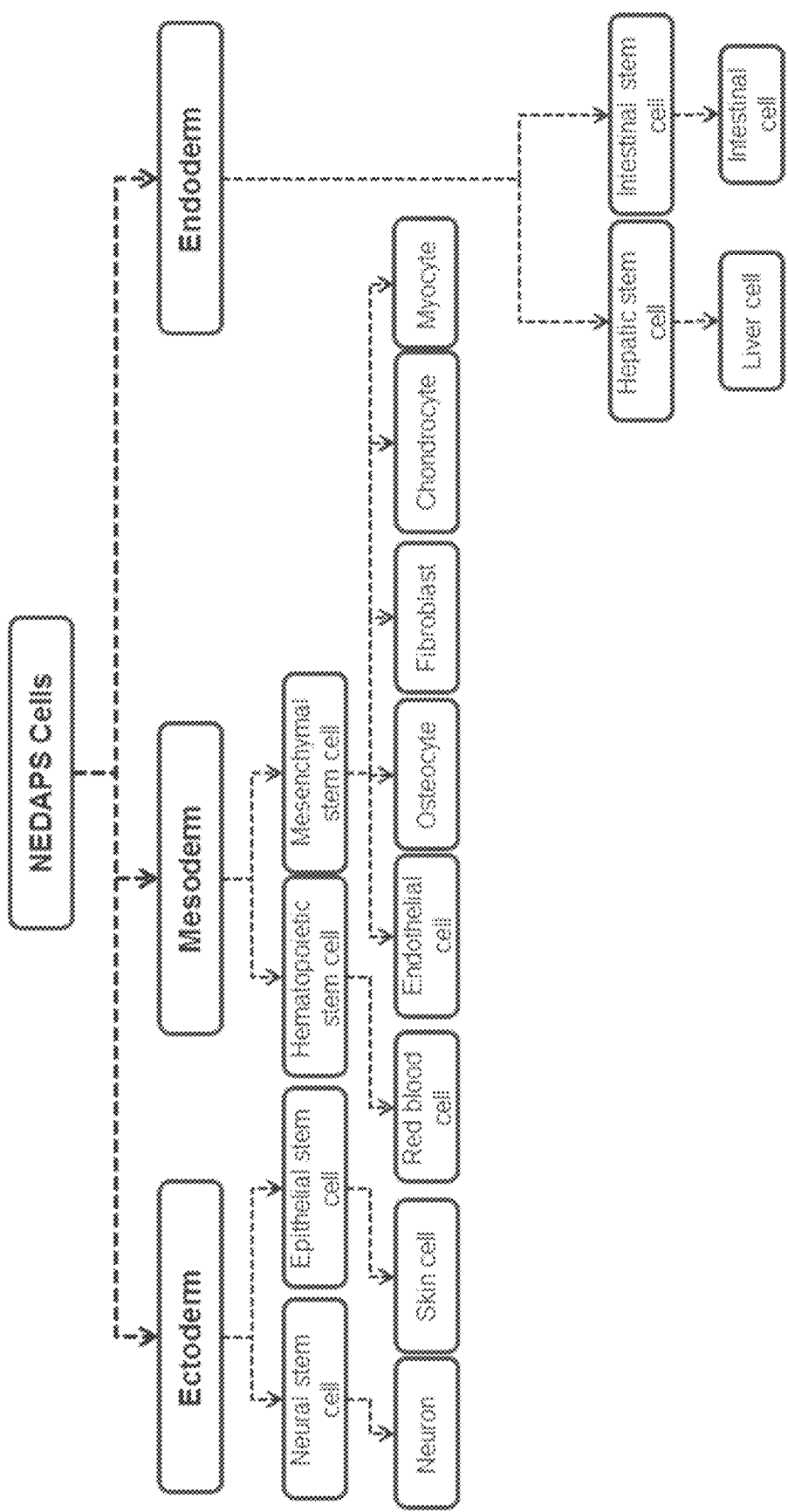

FIG. 18 illustrates exemplary pathways that the NEDAPS cells of the disclosure can be differentiated into. The illustration is abbreviated and does not show every possible cell type or intermediate cell type along each differentiation pathway. For example, hematopoietic stem cells can differentiate into myeloid and lymphoid progenitor cells, which give rise to the myeloid lineage (including red blood cells as shown in FIG. 18 as well as neutrophils, mast cells, etc.) and lymphoid lineage (which includes lymphocytes and natural killer cells), respectively.

7. DETAILED DESCRIPTION

7.1. Mammalian Peripheral Nerve-Derived Stem Cells (NEDAPS Cells)

The present disclosure provides Nerve derived adult pluripotent stem cells (NEDAPS cells) and populations thereof. As used in the context of "NEDAPS", the term "adult" refers to a non-embryonic source. Therefore, the NEDAPS cells can be from a juvenile or adult subject, and the subject can be a mammal, for example, a mouse, a rat, a domesticated mammal such as a cat, dog, rabbit, sheep, pig, cow, goat, or horse, or a primate such as a monkey or human.

The NEDAPS cells of the disclosure express the four transcription factors Oct4 (also known as Oct3/4 and POU5F1), Sox2, c-Myc, and Klf4. The gene sequences of these four transcription factors are highly conserved between mammalian species (Fritz et al., *Journal of Biological Chemistry* (2004) vol. 279(47): 48950-48958; Frankenberg et al., *Developmental Biology* (2010) vol. 337: 162-170; Rodda et al., *Journal of Biological Chemistry* (2005) vol. 280(26): 24731-24737; Flynn et al., *Molecular and Cellular Biology* (1998) vol. 18(10): 5961-5969; Stewart et al., *Virology* (1986) 154(1):121-34; Eladari et al., *Biochem* and Biophysical Res. *Communications* (1986) vol. 104(1):313-9). Further, somatic cells from mouse, human, rat, and rhesus monkey have been successfully reprogrammed into iPS cells capable of differentiating into all three germ layers (ectoderm, endoderm, and mesoderm) by inducing expression of these same, identical four factors. Takakashi and Yamanaka, *Cell* (2006) 126(4):663-76; Takahashi et al., *Cell* (2007) 131(5): 861-872; Liu et al., *Cell Stem Cell* (2008) 3:587-590; Liao et al., *Cell Stem Cell* (2009) 4(1):11-15. NEDAPS cells of the disclosure can also express the stem cell markers Nanog and SSEA1. Preferably, the expression of the transcription factors is not recombinant (e.g., not achieved via introduction of one or more expression vectors encoding one or more of the transcription factors).

The NEDAPS cells of the disclosure are capable of differentiating into mesoderm cells (e.g., mesenchymal cells, such as osteoblasts or endothelial cells), endoderm cells, and ectoderm cells (e.g., neural stem cells) when cultured under appropriate differentiation conditions. Examples of cell types into which the NEDAPS cells can be differentiated are shown in FIG. 18. Differentiation conditions for various cell type are known in the art and differentiation media are available commercially. Exemplary differentiation conditions described in section 7.2.3.

In certain embodiments, NEDAPS cells are motile both in vivo and in vitro (as evidenced by, for example, cell migration in vivo and migration of recently divided cells in vitro), readily adhere to glass or plastic substrate, and/or only infrequently form colonies.

The NEDAPS cells of the disclosure or their partially or completely differentiated progeny can be made recombinant or genetically engineered, e.g., to incorporate a heterologous gene from another species, a homologous gene from the same species (for example, to replace a gene that is mutant in the subject from whom the NEDAPS cells are derived), to express an engineered protein whose function is improved or altered relative to a wild type protein, or to incorporate a marker (e.g., a detectable marker or nucleic acid tag) to permit identification of the NEDAPS cells or their progeny, for example to track their fate following implantation. Nucleic acids can be introduced into a NEDAPS cell using methods known to persons skilled in the art (e.g., by the methods described in Wang and Gao, Discov Med. (2014) vol. 18 (97):67-77, the contents of which are incorporated by reference herein), and can be incorporated into the genomic DNA or not incorporated into the genomic DNA of the NEDAPS cell. For example, nucleic acids can be introduced into a NEDAPS cell by a recombinant virus (e.g., a retrovirus or a lentivirus), injection of naked DNA, or transfection (e.g., by a method using calcium phosphate, liposomes, or electroporation).

In another aspect, the disclosure provides NEDAPS cells, populations of NEDAPS cells, and cells and populations of cells differentiated therefrom, e.g., mesoderm cells (such as mesenchymal stem cells, osteoblasts, and endothelial cells), endoderm cells, or ectoderm cells (such as neural stem cells). In various aspects of the disclosure, a population is characterized by one, two, or all three characteristics:

(a) it is isolated; and/or
(b) it is at least 50% homogenous; and/or
(c) it contains at least 10 cells.

In particular embodiments of characteristic (b above, the population is at least 55%, at least 60%, at least 70%, at least 75%, at least 80%, at least 85%, at least 90%, at least 95%, at least 99%, or more than 99% homogeneous, e.g., for a population of NEDAPS cells that is at least 80% homogeneous, at least 80% of the cells in the population are NEDAPS cells. In particular embodiments of characteristic (c) above, the population contains at least 50 cells, at least 100 cells, at least 200 cells, at least 500, at least 1,000 cells or at least 10,000 cells. The disclosure is also directed to any and all permutations of the foregoing embodiments of characteristics (b) and (c) is, e.g., the population is at least 75% homogeneous and contains at least 200 cells, or the population is at least 60% homogeneous and contains at least 100 cells, or the population is at least 90% homogeneous and contains at least 50 cells.

7.2. Methods of Producing NEDAPS Cells and Cells Differentiated from NEDAPS Cells

7.2.1. NEDAPS Cell Proliferation Conditions

The present disclosure provides methods of producing NEDAPS cells and populations thereof both in vivo and ex vivo. NEDAPS cells and populations of NEDAPS cells can be produced by culturing a peripheral nerve exposed to NEDAPS cell proliferation conditions ex vivo or by culturing cells from a peripheral nerve exposed to NEDAPS cell proliferation conditions in a subject in vivo. In the context of ex vivo production of NEDAPS cells, the term "peripheral nerve" includes peripheral nerves that have been disrupted as described herein. Nerves suitable for generating NEDAPS cells include peripheral nerves that are routinely harvested surgically for nerve grafts subjects who have sustained an injury to a functionally important nerve. There are several such easily accessible nerves that can be harvested with minimal, if any, loss of function. The peripheral nerve can be, for example, a sural nerve, a branch of a sural nerve, a proper digital nerve of a finger or toe, a gracilis branch of an obturator nerve, a segment of a medial antebrachial cutaneous nerve, a lateral antebrachial cutaneous nerve, a proximal third webspace fascicle nerve, a posterior intraosseous nerve or other peripheral nerve.

NEDAPS cell proliferation conditions can comprise exposing the peripheral nerve to a cytokine such as a member of the bone morphogenic protein (BMP) family of cytokines. A preferred BMP protein for use in producing NEDAPS cells is BMP2, such as recombinant human BMP2 (rhBMP2). rhBMP2 is marketed by Medtronic as INFUSE®, and is FDA approved for stimulating bone formation. Studies have suggested that BMP2 induces neuroinflammation, and it is thought that this neuroinflammation may be basic to the process of BMP2-induced bone formation. Heggeness, *The Spine Journal*, (2011) 11:506. Similar neuroinflammatory responses following BMP2 exposure have been observed in mouse, rat, and human. See, e.g., Carragee et al., *The Spine Journal*, (2011) 11:471-491; Dmitriev et al., *The Spine Journal*, (2011) 11:500-505; Salisbury et al., *Journal of Cellular Biochemistry* (2011) 112:2748-2758. NEDAPS cells can be produced in vivo in a subject by directly applying a solution of BMP2 (e.g., a saline solution containing BMP2) to a surgically exposed peripheral nerve or by intramuscular (IM) injection to a site in the vicinity of a peripheral nerve.

BMP2 can be directly applied to an exposed nerve or injected to a site in the vicinity of a peripheral nerve, typically in an amount ranging from 10 ng to 1 mg. In some embodiments, the amount of BMP2 is 10 ng, 25 ng, 40 ng, 50 ng, 60 ng, 75 ng, 100 ng, 150 ng, 200 ng, 250 ng, 300 ng, 400 ng, 500 ng, 750 ng or 1 mg, or selected from a range bounded any pair of the foregoing values, e.g., 10 ng to 250 ng, 40 ng to 75 ng, 50 ng to 300 ng, 60 ng to 150 ng, and so on and so forth. The amount of BMP2 directly applied to an exposed nerve or injected to a site in the vicinity of a peripheral nerve can be provided in a solution having a volume ranging from 1 µl to 10 ml. In some embodiments, the volume is 0.1 ml to 2 ml, e.g., 0.25 ml, 0.5 ml 0.75 ml, 1 ml, 1.25 ml, or selected from a range bounded by any pair of the foregoing values, e.g., 0.1 ml to 1 ml, 0.25 ml to 1 ml, or 0.5 ml to 1.5 ml, and so on and so forth. The amount of BMP2 applied and the volume of BMP2 solution used can be varied depending on the size of the peripheral nerve targeted.

Alternatively, NEDAPS cells can be produced in vivo by exposing the subject to conditions that result in local production of BMP2, such as a bone fracture, blunt injury, thermal injury, or electric shock. In some embodiments, NEDAPS cells are obtained from a subject who has suffered a bone fracture, blunt injury, thermal injury, or electric shock.

NEDAPS cell proliferation conditions can also comprise exposing the peripheral nerve to a neuroinflammatory agent other than or in addition to BMP2, such as tumor necrosis factor alpha, Interleukin-1Beta, nerve growth factor, histamine, Interleukin 6, or a combination thereof.

In other embodiments, NEDAPS cell proliferation conditions comprise applying trauma to a peripheral nerve (in vivo or ex vivo). The trauma can be, for example, mechanical trauma, e.g., compressing the peripheral nerve (e.g., for 1-2 seconds), cutting or severing the peripheral nerve, or mincing the peripheral nerve, electrical stimulation (e.g., overstimulation), an ultrasonic shock wave, or a thermal insult. As such, in one aspect of the present disclosure, production of NEDAPS cells can be stimulated by subjecting peripheral nerve tissue to physical injury.

NEDAPS cell proliferation can also be achieved by exposing the peripheral nerve to BMP2 ex vivo by culturing the nerve in a medium comprising BMP2 and/or by subjecting the nerve to mechanical trauma (e.g., compression and/or mincing). In some embodiments, the concentration of BMP2 in the medium is 5 ng/ml, 10 ng/ml, 25 ng/ml, 40 ng/ml, 50 ng/ml, 60 ng/ml, 75 ng/ml, 100 ng/ml, 150 ng/ml, 200 ng/ml, 250 ng/ml, 300 ng/ml, 400 ng/ml, 500 ng/m, 750 ng/ml or 1 mg/ml, or selected from a range bounded any pair of the foregoing values, e.g., 5 ng/ml to 50 ng/ml, 10 ng/ml to 250 ng/ml, 40 ng/ml to 75 ng/ml, 50 ng/ml to 300 ng/ml, 60 ng/ml to 150 ng/ml, and so on and so forth.

Combinations of NEDAPS cell proliferation conditions described herein can also be used to produce NEDAPS cells. For example, NEDAPS cells can be produced by exposing a peripheral nerve to a combination of two or three of BMP2, compression, and mincing. In an embodiment, the NEDAPS cell proliferation conditions comprise mincing the peripheral nerve with or without exposure to BMP2.

The methods of the disclosure for producing NEDAPS cells can be practiced using human subjects and domesticated animals with minimal morbidity by the identification and use of suitable peripheral nerves. Examples of suitable nerves for human and veterinary applications are the sural nerve or one of its branches, a proper digital nerve to a central digit in the hand or foot, and a nerve from a limb amputated due to, for example, injury or disease. In cases of major trauma where portions of an extremity are to be amputated or discarded, or where nerves are injured beyond repair, such nerves can be harvested and used to generate NEDAPS cells, which can in turn be used for regenerative procedures and processes for that subject (i.e., in an autologous implantation procedure), or for a closely matched subject (i.e., in a closely matched but allogeneic implantation procedure). This technique would be particularly desirable for generating individual genetic "perfect match" cells for tissue engineering and other regenerative therapies in both human and veterinary applications.

7.2.2. Nerve Harvest and NEDAPS Cell Culture

The peripheral nerve of a subject exposed to NEDAPS cell proliferation conditions in vivo can be harvested, e.g., by surgical excision, from the subject immediately after exposure to NEDAPS cell proliferation conditions or can be harvested after a period of time. In some embodiments, the peripheral nerve is harvested up to 4 days, more preferably up to 3 days after exposure to NEDAPS cell proliferation conditions. For example, the peripheral nerve can be harvested about e.g., about 8 hours (or a third of a day), about 12 hours (or half a day), about 24 hours (or one day), about 48 hours (or two days), or about 72 hours (or three days) after exposure to NEDAPS cell proliferation conditions, or after a period selected from a range bounded by any pair of the foregoing values, e.g., 8 hours to 72 hours (or one third of a day to three days), 8 to 12 hours (or one third of a day to half a day), 12 to 24 hours (or half a day to a day), 24 to 48 hours (or one to two days), or 48 to 72 hours (or two to three days) after exposure to NEDAPS cell proliferation conditions, and so on and so forth. Following harvest, the nerve can optionally be disrupted to facilitate egress of the NEDAPS cells from the nerve.

Peripheral nerves exposed to NEDAPS cell proliferation conditions ex vivo can be cultured for a period of time after being exposed to NEDAPS cell proliferation conditions and can be optionally disrupted, either before or after culturing. In some embodiments, a peripheral nerve exposed to NEDAPS cell proliferation conditions ex vivo is cultured ex vivo for up to 4 days, more preferably up to 3 days following exposure to NEDAPS cell proliferation conditions, e.g., about 8 hours (or a third of a day), about 12 hours (or half a day), about 24 hours (or one day), about 48 hours (or two days), or about 72 hours (or three days), or for a period selected from a range bounded by any pair of the foregoing values, e.g., from 8 hours to 72 hours (or from one third of a day to three days), from 8 to 12 hours (or from one third of a day to half a day), from 12 to 24 hours (or from half a day to a day), from 24 to 48 hours (or from one to two days), or from 48 to 72 hours (or from two to three days), and so on and so forth.

Mechanical and/or enzymatic means can be used to disrupt a peripheral nerve. For example, the nerve can be minced, strained and/or subject to treatment with one or more proteases such as trypsin, a collagenase (e.g., a c. *histolyticum* collagenase), or matrix metalloprotease.

In some embodiments, the cells from a peripheral nerve are cultured in a medium comprising BMP2 after the peripheral nerve has been compressed, harvested, and disrupted by mincing and/or treatment with one or more proteases. In a preferred embodiment, cells from a peripheral nerve are cultured in a medium comprising BMP2 after the peripheral nerve has been compressed, harvested, and disrupted by mincing and treatment with one or more proteases.

A harvested peripheral nerve, cells from a disrupted peripheral nerve, and isolated NEDAPS cells can be cultured in a non-differentiating medium to maintain the NEDAPS cells in an undifferentiated state. Example 3 describes a suitable medium for culturing NEDAPS cells in a non-differentiated state. Other suitable non-differentiating media are known in the art, many of which are commercially available, e.g., Knockout™ DMEM (Gibco, catalog no. 10829-018) and mTeSR™1 medium (Stemcell Technologies, catalog no. 05857). NEDAPS cells can be cultured from a peripheral nerve without isolating the NEDAPS cells from other cell types present in the nerve. Alternatively, single or multiple NEDAPS cells can be separated from one or more other cell types, e.g., by micromanipulation, flow cytometry, or other methods for sorting or separating cells known in the art, and cultured to generate a population or expanded population of NEDAPS cells.

Following exposure of the nerve to NEDAPS cell proliferation conditions, the NEDAPS cell population can be maintained in undifferentiated form standard media or differentiated in a less potent cell type, for example as described in section 7.2.3. The differentiation can be carried out immediately after exposure to proliferation conditions or after maintenance of the NEDAPS cells in undifferentiated form.

7.2.3. Stem Cell Differentiation

A population of NEDAPS cells can be differentiated into a less potent cell type by exposing the population to differentiation conditions, for example, by culturing the population in a differentiation medium (or media) that induces stem cells to differentiate into a particular cell type. The NEDAPS cells of the disclosure can be differentiated into cells of the endodermal, mesodermal, and ectodermal lineages. Particular examples of cell types into which the NEDAPS cells can be differentiated are shown in FIG. 18. Differentiation conditions for various cell types are known in the art and differentiation media are available commercially, such as those for differentiating ESCs or iPS cells. Exemplary methods and media are described in Examples 4-6. For example, the StemXVivo™ Ectoderm Kit (R&D Systems, catalog #SC031), StemXVivo™ Mesoderm Kit (R&D Systems, catalog #SC030), and StemXVivo™ Endoderm Kit (R&D Systems, catalog #SC019) can be used to differentiate the NEDAPS cells into ectoderm, mesoderm, and endoderm cells, respectively, the media described in Example 4 can be used to differentiate a population of NEDAPS cells into osteoblasts or endothelial cells (i.e. two mesenchymal cell types), the media described in Example 5 can be used to differentiate a population of NEDAPS cells into endoderm cells, and the media described in Example 6 can be used to differentiate a population of NEDAPS cells into neural stem cells (i.e., an ectoderm cell type).

7.3. Uses

The methods described herein can be used to generate populations of NEDAPS cells and cell types differentiated therefrom, e.g., a population that is characterized by (a) being isolated and/or (b) being at least 50% homogenous and/or (c) containing at least 10 cells, and any of the embodiments thereof as described in Section 7. The populations find particular advantage for autologous applications, i.e., for implantation in the (human or other animal) subject from which the NEDAPS cells were derived.

NEDAPS cells and their differentiated progeny can be manipulated ex vivo to generate cells for treatment of a subject. The cells can be used for any condition that benefits from cell or organ regeneration. Particular applications include organ culture, wound healing, e.g., to treat diabetic lower extremity wounds, Charcot arthropathies, pressure ulcers, or bone fractures, nerve regeneration, restoring immune function, hematopoiesis, tissue engineering, gene therapy (e.g., as described in Wang and Gao, Discov Med. (2014) vol. 18 (98):151-161, the contents of which are incorporated by reference herein) and any other medical situation where stem cells grown in culture and induced to differentiate are useful.

In an embodiment, undifferentiated NEDAPS cells or osteoblasts differentiated from NEDAPS cells can be grown in vitro, and then placed into a site where bone formation is desired, such as a fracture site, a segmental bone defect site (e.g., after a tumor excision) or a site where bone ingrowth into an implant (e.g., an artificial joint component) is desired. In another embodiment, undifferentiated NEDAPS cells or endothelial cells that have been differentiated from NEDAPS cells can be propagated in culture, and then placed surgically or injected into an anatomic area where blood vessel formation is desired, such as a limb with a compromised blood supply. In another embodiment, fibroblasts differentiated from NEDAPS cells can be propagated in culture, then placed into an anatomic area where soft tissue healing is desired, for example, for treating a slow healing wound such as a diabetic foot ulcer. In another embodiment, hematopoietic cells differentiated from NEDAPS cells can be injected into the circulation or into the bone marrow of a subject with anemia. The injected hematopoietic cells can then produce blood cells for the subject.

The NEDAPS cells of the disclosure can also be used to evaluate toxicity of pharmaceutical compounds and other chemicals by, for example, using the NEDAPS cells in the methods described in U.S. Pat. No. 8,703,483, the contents of which are incorporated by reference herein.

The NEDAPS cells and cells differentiated therefrom can be made recombinant, for example for use in gene therapy.

For implantation into a subject, a population of NEDAPS cells or cells differentiated therefrom can be formulated in a pharmaceutically acceptable medium or excipient or a biocompatible and/or biodegradable scaffold or matrix.

8. EXAMPLES

8.1. Example 1: Production of NEDAPS Cells Using BMP2

Materials and methods: Ten mice were anaesthetized (under an IACUC approved protocol) and the right sciatic nerve was exposed using standard methods. In 7 animals, 50 nanograms of BMP2 was placed directly on the nerve. In 3 control animals, no agent was applied to the nerve.

Animals were humanely sacrificed after 12, 24 or 48 hours, and the sciatic nerve re-exposed and harvested. Nerves were fixed in formaldehyde and embedded in paraffin and sectioned by standard methods.

Figure 1A:
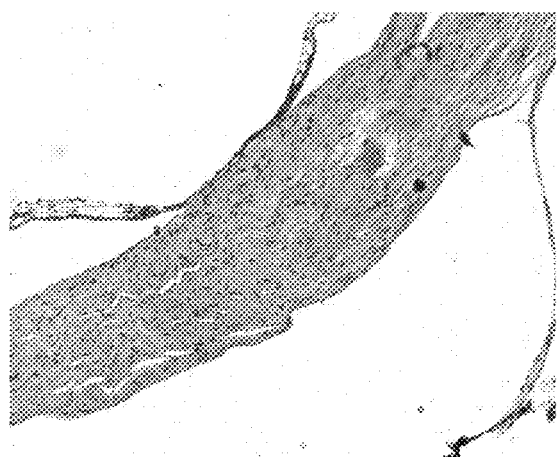
Figure 1B:
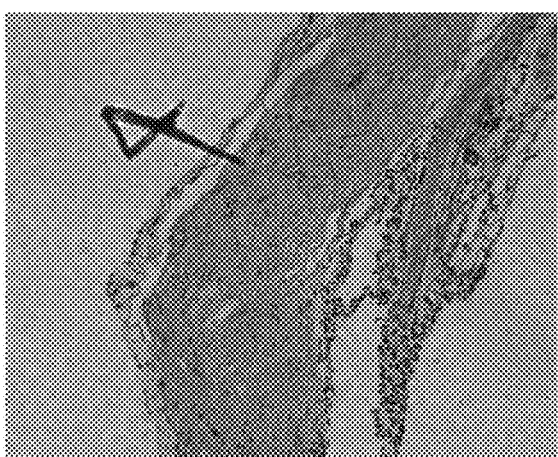
Figure 1C:
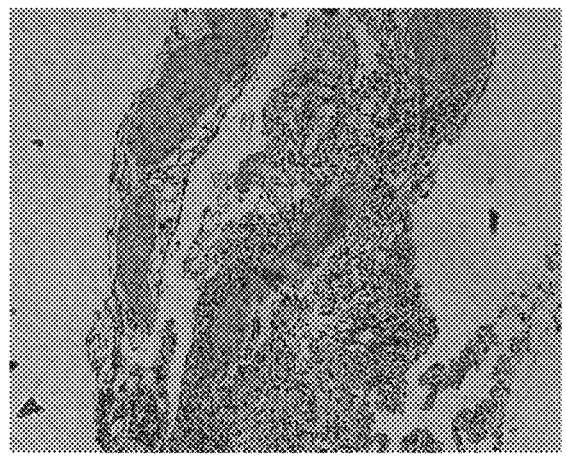
Figure 1D:
Figure 1E:
Figure 1F:
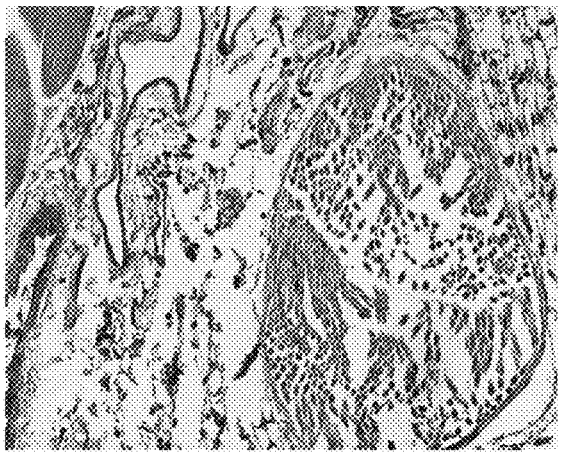
Figure 1G:
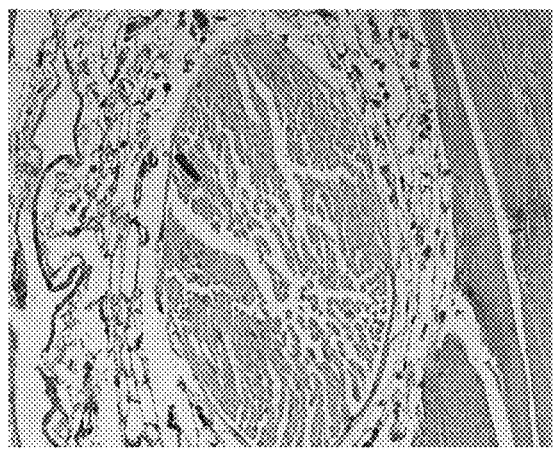
Figure 1H:
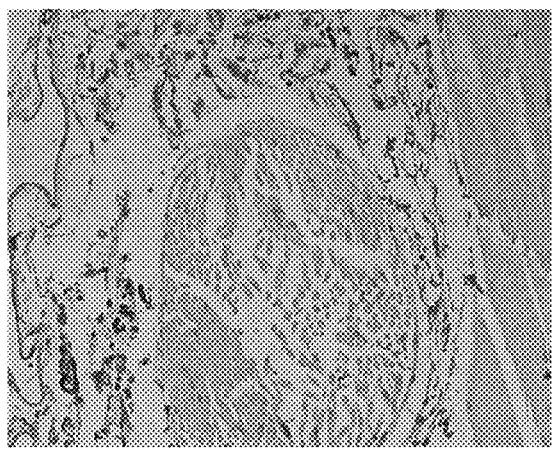
Figure 1I:
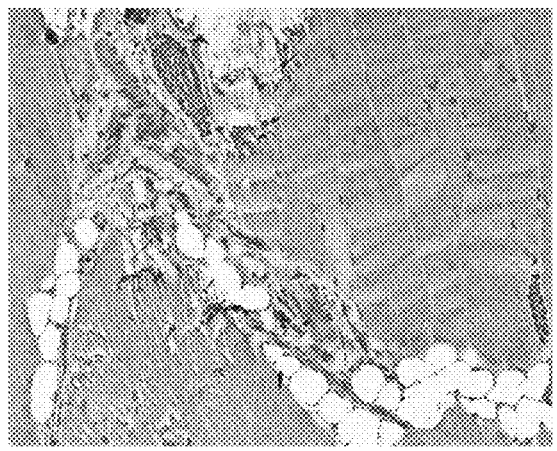
Figure 1J:
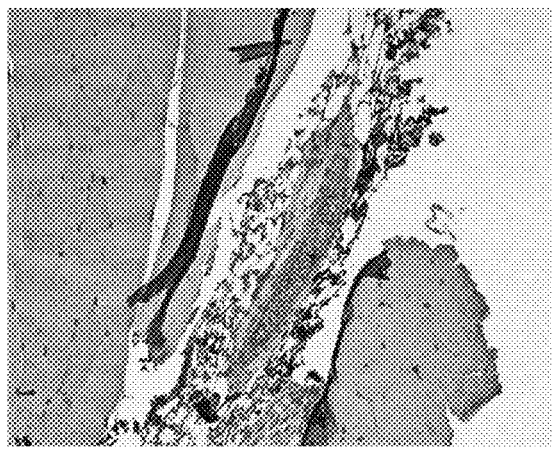
Figure 1K:
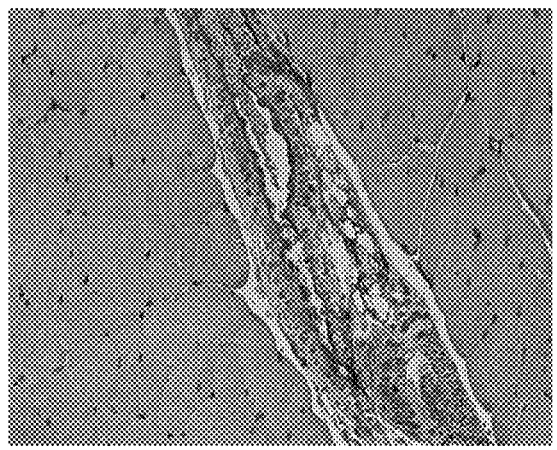
Figure 1L:
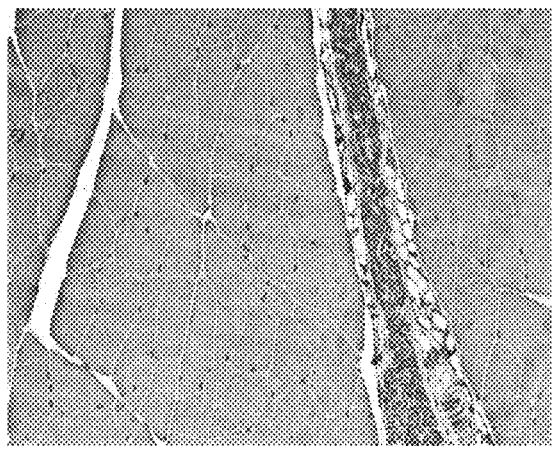
Figure 1M:
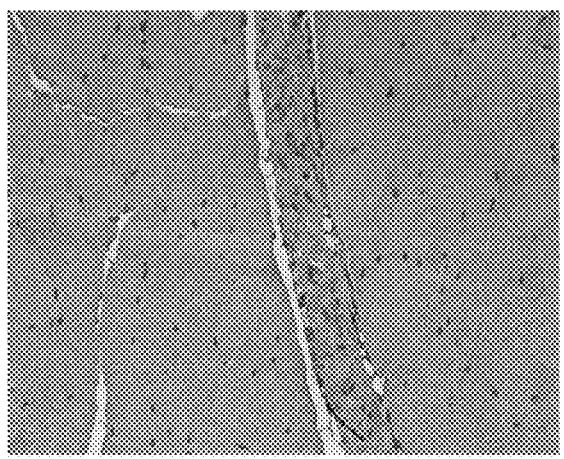
Figure 1N:
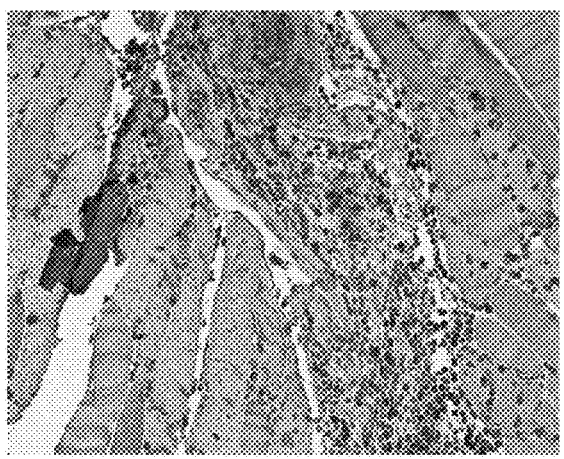

Results: The untreated nerves appeared normal (see FIG. 1A), with the exception of perhaps some mild inflammatory findings, thought to be due to the surgical exposure.

The BMP2 treated nerves were found to be fragmented and disrupted (see FIG. 1), but marked proliferation of cells were noted within the nerves. The treated nerves were noted to fragment spontaneously during and after the sectioning process. The nerves treated with BMP2 were abnormal and very fragile.

8.2. Example 2: Production of NEDAPS Cells Using IM Injected BMP2

Materials and Methods:

Twenty mice were anaesthetized and 50 ng or 100 ng of BMP2 were injected percutaneously (IM) into the right hamstring muscle of each mouse. The mice were sacrificed at 24, 48, or 72 hours. Hamstring muscles were harvested without dissecting down to the sciatic nerve, but taking care that the harvested tissue contained the usual anatomic location of this nerve. The contralateral (untreated) hamstring muscles were harvested from 4 animals to serve as control tissue.

Because the BMP2 was administered by IM injection, it was difficult to know after tissue harvest and processing how close the site of injection was to any given microscopic field. The sections were stained for an array of stem cell markers and a panel of inflammatory markers.

Figure 2A:
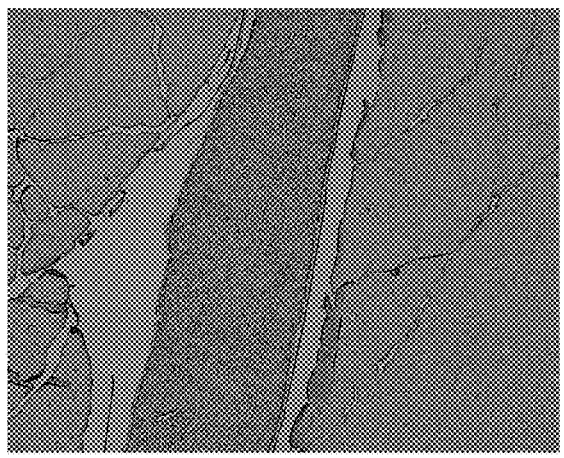
Figure 2B:
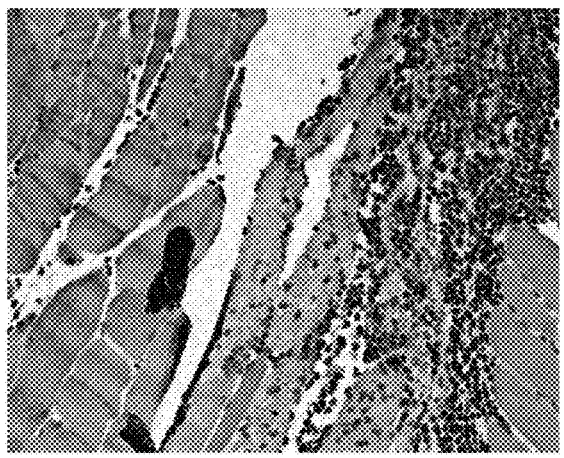
Figure 2C:
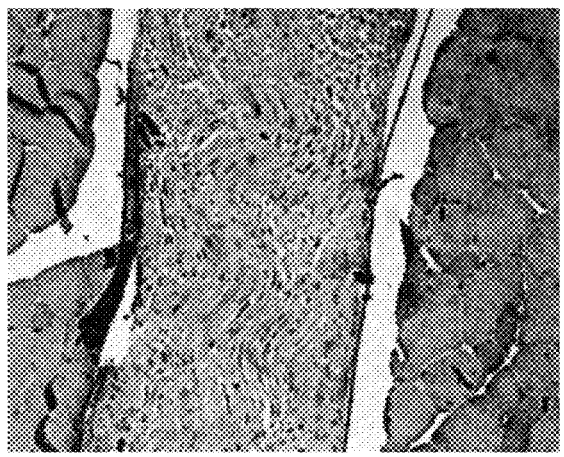
Figure 2D:
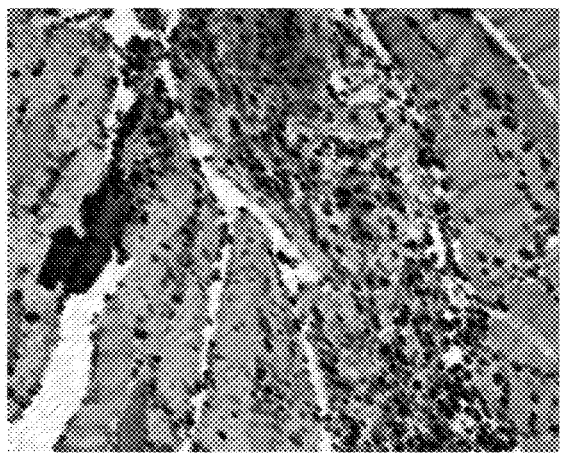
Figure 2E:
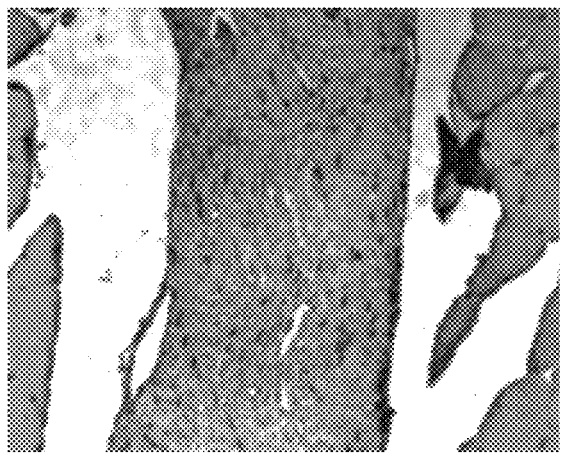
Figure 2F:
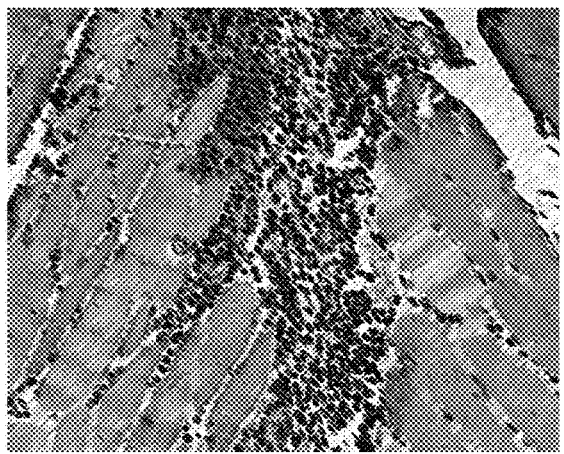
Figure 2G:
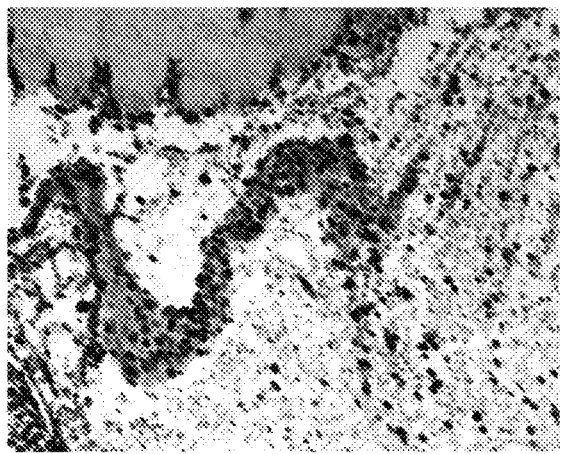
Figure 5:
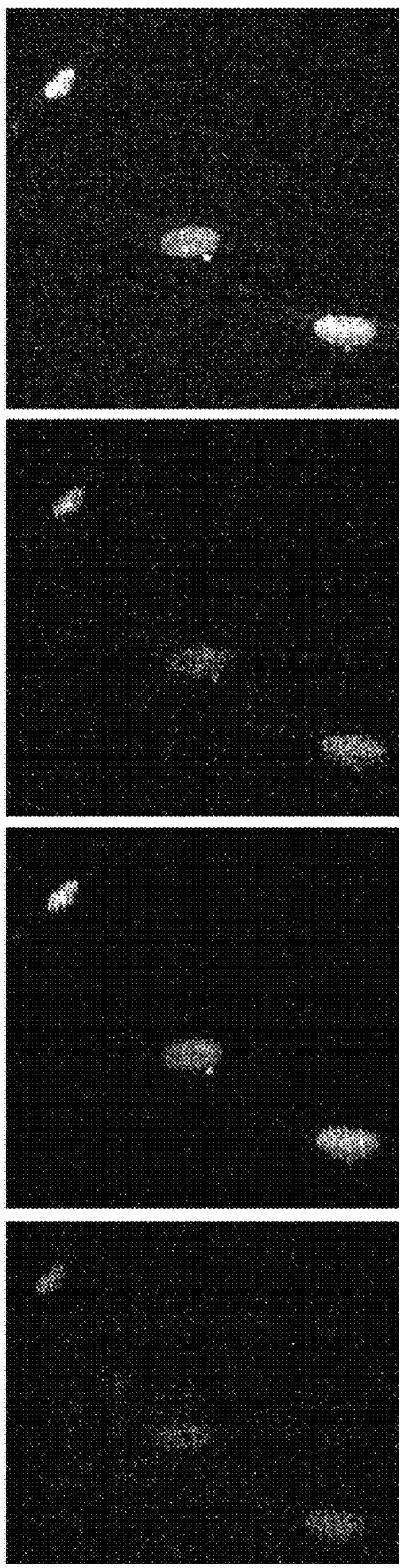
FIG. 5 shows NEDAPS cells produced using mechanical compression stained for the nonspecific nuclear stain DAPI (left panel), Klf4 (second panel from left), and c-Myc (third panel from left). The right panel is an overlay of the DAPI, Klf4 and c-Myc images.
Figure 6:
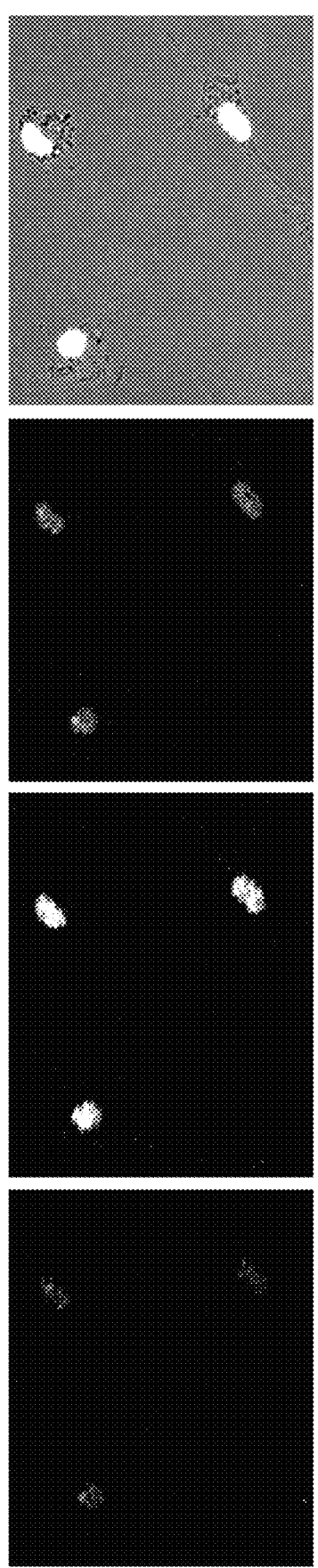
FIG. 6 shows NEDAPS cells produced using mechanical compression stained for the nonspecific nuclear stain DAPI (left panel), Klf4 (second panel from left), and Oct4 (third panel from left). The right panel is an overlay of the DAPI, Klf4 and Oct4 images.
Figure 7:
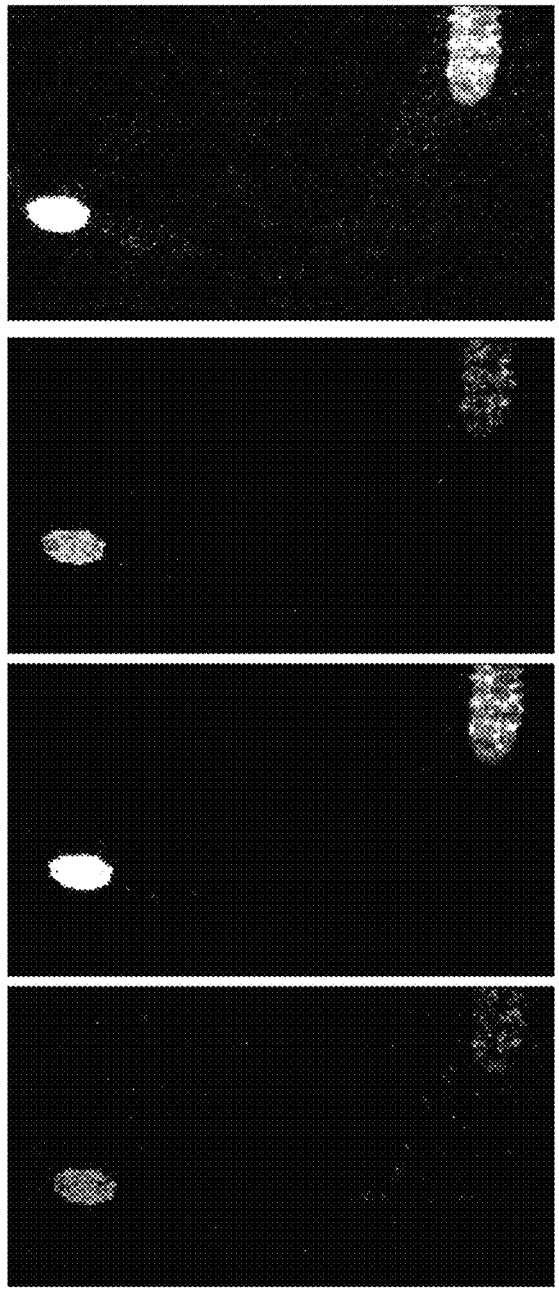
FIG. 7 shows NEDAPS cells produced using mechanical compression stained for the nonspecific nuclear stain DAPI (left panel), Sox2 (second panel from left), and Klf4 (third panel from left). The right panel is an overlay of the DAPI, Sox2 and Klf4 images.
Figure 8:
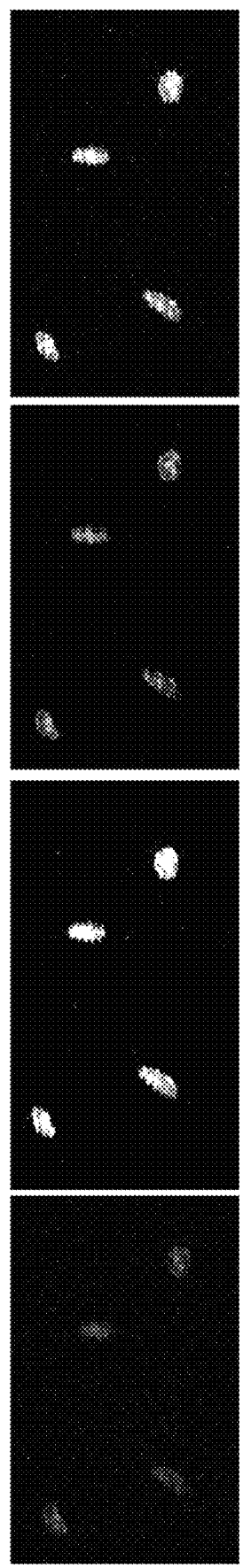
FIG. 8 shows NEDAPS cells produced using mechanical compression stained for DAPI (left panel), Oct4 (second panel from left), and c-Myc (third panel from left). The right panel is an overlay of the DAPI, Oct4 and c-Myc images.

Results:

The nerves from limbs injected with BMP2 appeared disrupted and slightly fragmented even in the 24 hour animals (see FIGS. 2B and 2D). The nerves from the treated animals displayed marked abnormalities by 72 hours (see FIG. 2F). The 72 hour specimens showed severely abnormal nerves. Universally, the abnormal nerves were expressing a preponderance of cells expressing all four ESC markers Oct4, Sox2, c-Myc, and Klf4.

A robust proliferation of cells within the nerve was seen consistently at 24 and 48 hours with the majority of these proliferating cells staining positive for all four ESC markers (see FIGS. 2B, 2D, 2F and 2G).

8.3. Example 3: NEDAPS Cell Production, Isolation and Culture

In Vivo NEDAPS Cell Production:

All animal activities were carried out in the Wichita State University Animal Care Facility and were approved by the Wichita State University Institutional Animal Care and Use Committee. 8 to 12 week-old female BALB/c mice were purchased from The Jackson Laboratory (Bar Harbor, Me.) and acclimated to the facility for at least 1 to 6 weeks prior to use in the study. On the day of surgery, the mice received 0.05 mg/kg of buprenorphine by subcutaneous injection one hour before surgery for preventative analgesia. The mice were anesthetized by intraperitoneal injection of 90 mg/kg ketamine and 8 mg/kg Xylazine, supplemented with 1-2% Isoflurane by nose cone. The right leg of each animal was shaved and the surgical area disinfected with Povidone-Iodine and ethanol. An incision was created on the lateral aspect of the thigh, and the sciatic nerve exposed by blunt dissection. The nerve was either manually compressed to approximately 25% of its original diameter using a forceps with a width of 1 mm at four or five sites along the length of the exposed nerve, or exposed to 60 ng of BMP2 in 10 µl of sterile saline (INFUSE® Bone Graft, Medtronic Spinal and Biologics, Memphis, Tenn.). The incision of each animal was sutured closed and the animal cared for, for 8, 24, 48, or 72 hours until sacrifice by $CO_2$ inhalation. The nerve was immediately harvested after sacrifice for histologic analysis, cell culture or screening for gene expression using polymerase chain reaction (PCR) methods.

Experiments were also performed using percutaneous injection of BMP2, into the hamstring muscle mass of the mouse posterior thigh. Identical anesthesia, analgesia and euthanasia were employed as above. Animals were sacrificed at 24, 48, and 72 hours post injection. Immediately post mortem, the hamstring muscle mass was harvested by sharp dissection and specimens were fixed in formalin, embedded in paraffin and sectioned. A total of 37 mice were treated by IM injection of 5 µl of sterile saline containing 60 ng of BMP2 (INFUSE®).

NEDAPS Cell Isolation and Culture:

NEDAPS cells were isolated from mouse sciatic nerves and cultured according to a published protocols (Wu et al., *Biotechnology letters* 2009; 31:1703-1708) with modifications. Briefly, sciatic nerve segments were minced to 1 mm pieces in PBS and pelleted by centrifugation at 600×g for 5 minutes. The nerve tissue was then incubated at 37° C. in 0.5 ml of 0.2% (0.27 U/ml) collagenase (Worthington Biochemical Corp) in sterile DMEM for 90 minutes, followed by addition of an equal volume of 0.05% trypsin-EDTA solution for 5 minutes with agitation. 300 µl of heat-deactivated fetal bovine serum (FBS) was added to the mixture to stop the enzyme digestion. After filter through a 100 µm-sized mesh, the isolated cells were centrifuged down at 600×g for 10 min. The cell pellets were resuspended and distributed to 6-well culture dishes, or 4-well chamber-slide in DMEM (Gibco, Life Technologies), supplemented with 20% Knockout serum replacement (KSR, Gibco), 100 µM MEM non-essential amino-acid solution (Gibco), 1× GlutaMAX™-1 (Cat. no. 35050-079, Gibco); 55 µM β-mercaptoethanol (Gibco), 20 ng/ml human leukemia inhibitory factor (LIF, Gibco), 100 U/ml penicillin (Invitrogen, Grand Island, N.Y.), and 100 µg/ml streptomycin (Invitrogen). The cells were cultured at 37° C., 5% $CO_2$ atmosphere.

NEDAPS Cell Characterization:

To characterize the NEDAPS cells, double stainings against a pair of ESC markers (Klf4, Sox2, Oct4, and c-Myc) were performed. Briefly, cells grown in chamber slides were fixed with 4% paraformaldehyde for 30 minutes at room temperature, washed 3× with PBS, and blocked with 3% normal donkey serum and 0.1% Triton X-100. Primary primer pairs for each target gene were designed using Primer3 program (bioinfo.ut.ee/primer3-0.4.0/primer3) and constructed by Sigma-Genosys (Woodlands, Tex.). The primer sequences are shown in Table 1.

TABLE 1

Primers Utilized for RT-PCR Amplification

| Target | Forward Primer | Reverse Primer | Product Size (bp) |
|---|---|---|---|
| Sox2 | aagggttcttgctgggtttt (SEQ ID NO: 1) | agaccacgaaaacggtcttg (SEQ ID NO: 2) | 150 |
| c-Myc | acccgctcaacgacagcagc (SEQ ID NO: 3) | ccgtggggaggactcggagg (SEQ ID NO: 4) | 104 |
| Klf4 | ctgaacagcagggactgtca (SEQ ID NO: 5) | gtgtgggtggctgttcttt (SEQ ID NO: 6) | 218 |
| Oct4 | gaggagtcccaggacatgaa (SEQ ID NO: 7) | agatggtggtctggctgaac (SEQ ID NO: 8) | 154 | antibodies include goat anti-Klf4 (R&D), goat anti-Sox2 (Santa Cruz Biotechnology), goat and rabbit anti-Oct4 (Abcom), and rabbit anti-c-Myc (Santa Cruz Biotechnology). Secondary antibodies used were donkey anti-goat IgG conjugated with Alexa 488, and donkey anti-rabbit IgG with Alexa Fluor® 594 (Life Technologies). Cells were double stained with primary goat- and rabbit-antibody pairs (Klf-4+c-Myc, Sox2+c-Myc, Klf-4+Oct4, and Sox2+OCT4) for 60 minutes at 37° C. After a PBS rinse, the cells were incubated in 1:200 secondary antibodies with distinct fluorescent wavelength for 30 minutes at 37° C., and coverslips were mounted onto the sections with DAPI Fluoromount G (SouthernBiotech) which also counterstained cell nuclei. Stained cells were viewed under a TCS SP5 II confocal laser scanning microscope (Leica Microsystems) and images acquired with the LAS Image Analysis optional software. Optical single sections were acquired with a scanning mode format of 1024×1024 pixels, with a pixel size of 0.21 μm. Acquisition of automated-sequential collection of multi-channel images was performed in order to reduce spectral crosstalk between channels, and individual images of double staining signals were overlaid to generate co-localized images.

Gene expression profiles of Klf-4, c-Myc, Sox2, and Oct4 among test groups were determined using RT-PCR techniques as detailed previously (Yang et al., J Bone Joint Surg Am. (2005) 87(5):1088-97.) Briefly, cells were homogenized in a 5-ml Dounce homogenizer in STAT-60™ (Tel-Test, Friendswood, Tex.) solution and the total RNA was isolated by chloroform separation and isopropanol precipitation. Complementary DNA (cDNA) was reverse transcribed from 0.5 g of total RNA in 40 μl PCR buffer containing 5.5 mM $MgCl_2$, 500 μM each of deoxynucleotide triphosphates, 0.5 U/μl RNase inhibitor, 2.5 μM random hexamers, and 1.25 U/μl reverse transcriptase (Perkin-Elmer Cetus, Norwalk, Conn.) on a Veriti 96-well Thermal Cycler (Applied Biosystems, Foster City, Calif.) at 25° C. for 10 minutes, 48° C. for 25 minutes, and 95° C. for 5 minutes. RT-PCR reaction mixtures contained SYBR Green PCR Master Mix (Applied Biosystems), 2 μl cDNA, and 400 nM tested gene primer pairs were run in a StepOnePlus® Real-Time PCR System (Applied Biosystems) for 40 cycles. The fluorescent signals were dynamically recorded. The Results:

Cultured NEDAPS cells expressed Klf4, Sox2, Oct4, and c-Myc, as shown in FIG. 3-9. The cells were observed to generally be quite flat and spread across the glass or plastic substrate (see FIG. 10), showing that the cells were adherent. The cells could not be "rinsed off" when the media was changed, also showing that the cells adhered to the substrate. Passaging the cells to a new plate required exposing them to trypsin to get them to detach.

8.4. Example 4: Osteogenic and Endothelial Cell Differentiation (Mesoderm Cell Differentiation)

Cell Culture:

After maintaining NEDAPS cells cultured in embryonic stem cell medium for 5 days, the cells were experimented for differentiation. For osteoblastic cell induction, NEDAPS cells were cultured with osteogenic medium containing 10 mM beta-sodium glycerophosphate, 50 μg/ml ascorbic acid and 10 nM dexamethasone in DMEM/F12 medium, plus 10% fetal bovine serum, 100 mg/ml streptomycin and 100 U/ml penicillin. Alkaline phosphatase staining and type I collagen staining were performed 7 days later to identify the structural and functional properties of the osteoblastic cells. NEDAPS cells directed for endothelial cell differentiation were plated onto flasks coated with fibronectin (Sigma-Aldrich, US) and cultured in endothelial cell basal medium-2 (Lonza Walkersville, Inc. Walkersville, Md.) supplemented with EGM™-2-MV SingleQuots™, containing 5% FBS, 10 ng/ml human epidermal growth factor (hEGF), 50 ng/ml human vascular endothelial growth factor (VEGF), 50 ng/ml human insulin-like growth factor-1 (IGF-1), 1 μg/ml hydrocortisone, and 100 U/ml penicillin (Invitrogen, US), and 100 μg/ml streptomycin (Invitrogen, US).

Characterization of Differentiated Cells:

A commercial alkaline phosphatase (ALP) staining Kit (Sigma-Aldrich, St. Louis, Mo.) was used for the semi-quantitative demonstration of alkaline phosphatase activity in the differentiated osteoblastic cells as described previously (Jiang et al., *J Biomed Mater Res A* (2013)101:2817-2825). Briefly, alkaline-dye mixture was prepared to dissolve the Fast Violet B capsule and Naphthol AS_MX Alkaline Phosphate in distilled water. After fixation in citrate buffered acetone for 30 seconds, cells were incubated in alkaline-dye mixture for 30 minutes at 26° C. followed by Mayer's Hematoxylin counterstain for 1 min. The resulting insoluble diffuse, red dye deposit within cytoplasm indicates alkaline phosphatase activity. Immunostaining for type I collagen was also performed.

Gene expression profiles for the osteoblastic markers osteopontin, type I collagen, and osteocalcin, and for endothelial markers Flt-1 and Flk-1 were determined using the RT-PCR techniques described in Example 3. The primers used are shown in Table 2.

TABLE 2

Primers Utilized for RT-PCR Amplification

| Target | Forward Primer | Reverse Primer | Product Size (bp) |
|---|---|---|---|
| Flt-1 (VEGFR-1) | ccaaggcctccatgaagata (SEQ ID NO: 9) | atactgtcaggggctggttg (SEQ ID NO: 10) | 248 |
| Flk-1 (VEGFR-2) | ttctggactctccctgccta (SEQ ID NO: 11) | tctgtctggctgtcatctgg (SEQ ID NO: 12) | 210 |
| Osteopontin | Qiagen catalog no. QT00157724 | Qiagen catalog no. QT00157724 | 92 |
| Collagen, type I | Qiagen catalog no. QT00162204 | Qiagen catalog no. QT00162204 | 98 |
| Osteocalcin | Qiagen catalog no. QT01744330 | Qiagen catalog no. QT01744330 | 77 |

Results:

Cells cultured in osteogenic medium expressed osteogenic markers osteopontin, type I collagen, and osteocalcin (see FIG. 11) and positively stained for alkaline phosphatase and for type I collagen (see FIG. 12-13), indicating that the NEDAPS cells had differentiated into osteoblastic cells. Cells cultured in endothelial medium had a morphology typical of endothelial cells, with a small rounded cell body and multiple long extended processes (see FIG. 14), and expressed endothelial markers Flt-1 and Flk-1 (see FIG. 11).

8.5. Example 5: Definitive Endoderm (DE) Induction

Cell culture: NEDAPS cells were induced into the DE lineage using a commercial kit from Gibco (Life Technologies). Briefly, NEDAPS cells were cultured in a 12-well plate with Gibco® Essential 8™ medium at 37° C., 5% $CO_2$. On day 1, Essential 8™ medium was replaced with pre-warmed DE Induction Medium A for 24 hours. On day 2, DE Induction Medium A was completely aspirated and replaced with pre-warmed DE Induction Medium B. The plate was incubated at 37° C. for 24 hours. Morphology changes of the cells were monitored under an inverted microscope.

Results:

Following culture in the DE induction medium, the growing cells were morphologically very different from the NEDAPS cells prior to induction. The cells become more rounded (i.e., less squamous) and displayed larger nuclei than undifferentiated NEDAPS cells (see FIG. 15), indicating clear differentiation away from NEDAPS cells and development of endodermal characteristics

8.6. Example 6: Differentiation of Neural Stem Cells (Ectoderm Cell Differentiation)

Cell Culture:

NEDAPS cells were propagated and induced to differentiate into neural stem cells. For proliferation of the cells, NEDAPS cells were cultured in Complete NeuroCult™ NSC Proliferation Medium that contained 10% NeuroCult™ NSC proliferation supplement (v/v) (Stemcell Technologies, catalog no. 05701) in NSC basal medium (Stemcell Technologies, catalog no. 05700). rhEGF at a final concentration of 20 ng/ml was also included in the cultures. When 30% cell confluence was reached, the medium was removed and replaced by Complete NeuroCult™ NSC Differentiation Medium that contained 10% NeuroCult™ NSC differentiation supplement (Stemcell Technologies, catalog no. 05703), and the culture was incubated at 37° C. for two days. Morphology changes of the cells were monitored under an inverted microscope.

Results:

Following culture in the differentiation medium, the cells had a very different morphology than the NEDAPS cells prior to differentiation. The cells had very elongated cell bodies (see FIG. 16), very different from the generally squamous cell morphology of the original NEDAPS cells. These elongated cells displayed features of primitive nerve cells, characteristic of ectoderm.

8.7. Example 7: One-Step Production of NEDAPS Cells

Materials and Methods:

Mouse sciatic nerves were surgically exposed and retrieved using sterile techniques. Gentle compressions were applied for 1-2 seconds along the nerves before dissecting out from the body. Nerve tissue was minced to 1 mm pieces and digested with collagenase and trypsin as described in Example 3. Cells were collected by centrifugation and placed into a 12-well culture plate or 8-well chamber slide in the stem cell medium described in Example 3. BMP2 was added to the medium 24 hours later at a final concentration of 750 ng/ml and cultured for 24 hours, after which this media was evacuated and replaced by the stem cell media described in Example 3: DMEM (Gibco, Life Technologies), supplemented with 20% Knockout serum replacement (KSR, Gibco), 100 µM MEM non-essential amino-acid solution (Gibco), 1× GlutaMAX™-I (Cat. no. 35050-079, Gibco); 55 µM β-mercaptoethanol (Gibco), 20 ng/ml human leukemia inhibitory factor (LIF, Gibco), 100 U/ml penicillin (Invitrogen, Grand Island, N.Y.), and 100 µg/ml streptomycin (Invitrogen). In all stages the cells were cultured at 37° C., in a 5% $CO_2$ atmosphere.

Cell Characterization:

The cells were stained for Klf4, Sox2, Oct4, and c-Myc.

Results: The cells produced using this method express the four embryonic stem cell markers Klf4, Sox2, Oct4, and c-Myc (see FIG. 17).

9. SPECIFIC EMBODIMENTS

The present disclosure is exemplified by the specific embodiments below.

1. A method for inducing production of stem cells in a peripheral nerve, the method comprising:
providing a subject;
exposing a selected peripheral nerve of the subject to an exogenous stimulus for a selected period of time;
after the selected period of time, harvesting stem cells from the stimulated peripheral nerve; and
culturing the embryonic stem cells in vitro in a non-differentiating medium.

2. The method of embodiment 1, wherein the stem cells are selected from the group consisting of totipotent cells, pluripotent cells, multipotent cells, oligopotent cells, unipotent cells, and combinations thereof.

3. The method of embodiment 1, wherein the exogenous stimulus is one or more of a physical injury, mechanical manipulation, disruption, an electrical stimulus, or exposure to a cytokine.

4. The method of embodiment 3, wherein the cytokine is a member of the bone morphogenic protein (BMP) family of cytokines.

5. The method of embodiment 4, wherein the cytokine is BMP2.

6. The method of embodiment 5, further comprising applying BMP2 to the peripheral nerve in situ to stimulate the proliferation of the stem cells;
surgically excising the peripheral nerve, and
culturing the stem cells in vitro in a non-differentiating medium to foster the proliferation of stem cells to create a population of stem cells.

7. The method of embodiment 3, further comprising applying the electrical stimulus the peripheral nerve in situ to stimulate the proliferation of stem cells;
surgically excising the peripheral nerve, and
culturing the stem cells in vitro in a non-differentiating medium to foster the proliferation of stem cells to create a population of stem cells.

8. The method of embodiment 1, further comprising exposing the stem cells in vitro to one or more differentiation factors to cause differentiation of the stem cells to form tissue progenitor cells.

9. The method of embodiment 8, further comprising reimplanting the tissue progenitor cells is a body of a subject.

10. The method of embodiment 9, wherein the subject is the donor of the peripheral nerve of embodiment 1.

11. The method of embodiment 1, further comprising:
harvesting the stimulated peripheral nerve from the subject; and
mechanically disrupting the nerve either before or after initiating the culturing to facilitate egress of the embryonic stem cells from the peripheral nerve.

12. The method of embodiment 11, wherein the mechanically disrupting includes one or more of mincing or dividing a sheath of the peripheral nerve.

13. The method of embodiment 1, further comprising:
harvesting the stimulated peripheral nerve from the subject; and
enzymatically treating the nerve either before or after initiating the culturing to facilitate egress of the stem cells from the peripheral nerve.

14. The method of embodiment 13, wherein the enzymatically treating includes treatment with a protease.

15. The method of embodiment 14, wherein the protease is at least one of a collagenase or a matrix metalloproteinase.

16. The method of embodiment 1, further comprising surgically excising at least a portion of a peripheral nerve from the subject;
exposing the surgically excised peripheral nerve to the exogenous stimulus for a selected period of time;
after the selected period of time, harvesting embryonic stem cells from the stimulated peripheral nerve; and
culturing the embryonic stem cells in vitro in a non-differentiating medium.

While various specific embodiments have been illustrated and described, it will be appreciated that various changes can be made without departing from the spirit and scope of the disclosure(s).

10. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A method of producing a population of mammalian nerve derived adult pluripotent stem cells expressing Oct4, Sox2, c-Myc and Klf4 from a non-embryonic peripheral nerve from a subject, said method comprising:
   providing a non-embryonic peripheral nerve exposed to NEDAPS cell proliferation conditions ex vivo or in vivo, wherein said non-embryonic peripheral nerve exposed to NEDAPS cell proliferation conditions comprises nerve derived adult pluripotent stem cells,
   culturing ex vivo said non-embryonic peripheral nerve or said nerve derived adult pluripotent stem cells from said non-embryonic peripheral nerve, and
   isolating cells expressing Oct4, Sox2, c-Myc, and Klf4 from culture to yield said population of mammalian nerve derived adult pluripotent stem cells,
   wherein said NEDAPS cell proliferation conditions comprise exposure of said non-embryonic peripheral nerve to a neuroinflammatory agent, trauma, or a combination thereof,
   wherein the neuroinflammatory agent is BMP2, tumor necrosis factor alpha, lnterleukin-1 Beta, nerve growth factor, histamine, Interleukin 6, or a combination thereof, and
   wherein the trauma is a mechanical trauma, an electrical stimulation, an ultrasonic shock wave, a thermal insult, or a combination thereof.

2. The method of claim 1, wherein the providing step comprises harvesting the non-embryonic peripheral nerve from the subject and exposing the non-embryonic peripheral nerve to the NEDAPS cell proliferation conditions ex vivo to yield said non-embryonic peripheral nerve comprising said nerve derived adult pluripotent stem cells.

3. The method of claim 1, wherein when the peripheral nerve is exposed to said NEDAPS cell proliferation conditions in said subject in vivo, said method further comprising harvesting the peripheral nerve prior to said culturing.

4. The method of claim 3, wherein the providing step comprises exposing the peripheral nerve to the NEDAPS cell proliferation conditions in vivo prior to the harvesting.

5. The method of claim 1, wherein the trauma is a mechanical trauma which comprises compressing the peripheral nerve, cutting the peripheral nerve, mincing the peripheral nerve, or a combination thereof.

6. The method of claim 1, wherein the peripheral nerve is disrupted prior to said culturing to release said nerve derived adult pluripotent stem cells from said peripheral nerve.

7. The method of claim 6, wherein the peripheral nerve is disrupted by treatment with a protease.

8. The method of claim 1, wherein the peripheral nerve is a sural nerve, a branch of a sural nerve, a proper digital nerve of a finger or toe, a gracilis branch of an obturator nerve, a segment of a medial antebrachial cutaneous nerve, a lateral antebrachial cutaneous nerve, a proximal third webspace fascicle nerve, or a posterior intraosseous nerve.

9. The method of claim 1, wherein the culturing comprises culturing the peripheral nerve or nerve derived adult pluripotent stem cells from the peripheral nerve in a non-differentiating medium.

10. A method of producing a population of differentiated cells, comprising exposing a population of mammalian nerve derived adult pluripotent stem cells produced by the method of claim 1 to differentiation conditions.

11. The method of claim 10, wherein the differentiated cells are mesoderm cells and the differentiation conditions comprise culturing the population in a mesoderm differentiation medium.

12. The method of claim 10, wherein the differentiated cells are endoderm cells and the differentiation conditions comprise culturing the population in an endoderm differentiation medium.

13. The method of claim 10, wherein the differentiated cells are ectoderm cells and the differentiation conditions comprise culturing the population in an ectoderm differentiation medium.

14. The method of claim 1, wherein said step of culturing comprises culturing said peripheral nerve, wherein the peripheral nerve is disrupted after said culturing to release said nerve derived adult pluripotent stem cells from said peripheral nerve prior to said isolating.

15. The method of claim 14, wherein the peripheral nerve is cultured in non-differentiating medium.

16. The method of claim 2, wherein said NEDAPS cell proliferation conditions comprise exposing said non-embryonic peripheral nerve to trauma, wherein said nerve derived adult pluripotent stem cells released from said peripheral nerve are further cultured in medium comprising BMP2 prior to said isolating.

17. The method of claim 2, wherein the non-embryonic peripheral nerve is exposed to the NEDAPS cell proliferation conditions in non-differentiating medium.

* * * * *